(12) United States Patent
Asfora et al.

(10) Patent No.: US 11,291,555 B2
(45) Date of Patent: Apr. 5, 2022

(54) VERTEBRAL CAGE

(71) Applicant: ASFORA IP, LLC, Sioux Falls, SD (US)

(72) Inventors: Wilson Theophilo Asfora, Sioux Falls, SD (US); Daniel S. Savage, Brecksville, OH (US)

(73) Assignee: Asfora IP, LLC, Sioux Falls, SD (US)

( * ) Notice: Subject to any disclaimer, the term of this patent is extended or adjusted under 35 U.S.C. 154(b) by 561 days.

(21) Appl. No.: 14/872,894

(22) Filed: Oct. 1, 2015

(65) Prior Publication Data

US 2017/0095349 A1 Apr. 6, 2017

(51) Int. Cl.
| | | |
|---|---|---|
| *A61F 2/44* | (2006.01) | |
| *A61F 2/30* | (2006.01) | |
| *A61B 17/86* | (2006.01) | |
| *A61B 17/70* | (2006.01) | |

(52) U.S. Cl.
CPC ............ *A61F 2/4455* (2013.01); *A61F 2/446* (2013.01); *A61B 17/7065* (2013.01); *A61B 17/86* (2013.01); *A61F 2/4425* (2013.01); *A61F 2002/3052* (2013.01); *A61F 2002/3085* (2013.01); *A61F 2002/30482* (2013.01); *A61F 2002/30507* (2013.01); *A61F 2002/30538* (2013.01); *A61F 2002/30579* (2013.01); *A61F 2002/30787* (2013.01)

(58) Field of Classification Search
CPC ... A61B 1/3132; A61B 17/86; A61B 17/7065; A61F 2/4455; A61F 2/446; A61F 2/442; A61F 2/4425; A61F 2/44; A61F 2002/30482; A61F 2002/30507; A61F 2002/30538; A61F 2002/30787; A61F 2002/3085; A61F 2002/448; A61F 2002/4638; A61F 2002/30484; A61F 2002/30018; A61F 2002/30571; A61F 2002/30565; A61F 2002/30556; A61F 2002/30509; A61F 2002/30471; A61F 2002/30579; A61F 2002/443; A61F 2002/30624; A61F 2002/4475; A61F 2002/30019; A61F 2002/30553; A61F 2002/3052; A61F 2002/445; A61F 5/0102
See application file for complete search history.

(56) References Cited

U.S. PATENT DOCUMENTS

| | | | | |
|---|---|---|---|---|
| 6,129,763 | A * | 10/2000 | Chauvin | A61F 2/446 623/17.11 |
| 6,436,142 | B1 * | 8/2002 | Paes | A61B 17/8615 623/17.15 |
| 6,471,724 | B2 * | 10/2002 | Zdeblick | A61B 17/282 623/17.16 |
| 6,849,093 | B2 * | 2/2005 | Michelson | A61F 2/446 623/17.11 |

(Continued)

*Primary Examiner* — Marcela I. Shirsat
(74) *Attorney, Agent, or Firm* — Fox Rothschild LLP

(57) ABSTRACT

Systems, methods and devices for spinal fusion are disclosed. In particular, certain disclosed embodiments are configured to permit the addition of lordosis to a spinal fusion cage after implantation through the use of various expansion mechanisms to spread arms of the spinal fusion cage. Disclosed embodiments may include the use of a threaded wedge to expand the arms, the use of a keel within a series of detents, the use of supplemental fixation screws, and the use of a rotating cam.

23 Claims, 20 Drawing Sheets

(56) References Cited

U.S. PATENT DOCUMENTS 7,217,293 B2 * 5/2007 Branch, Jr. ............. A61F 2/447
 623/17.11
7,431,735 B2 * 10/2008 Liu ......................... A61F 2/446
 623/17.11
7,655,046 B2 * 2/2010 Dryer ...................... A61F 2/446
 623/17.11

* cited by examiner

VERTEBRAL CAGE

FIELD

The present application relates to medical devices. More specifically, the application relates to vertebral cage devices configured to at least partially expand to impart lordosis.

BACKGROUND

Lordosis is the natural curvature of the lumbar and cervical regions of the spine. Certain spinal fusion procedures may result in an undesirable loss of lordosis. Loss of lordosis may cause negative posture changes and back pain. Therefore, there is a need for systems, devices, and techniques to perform spinal fusion procedures while preserving lordosis.

BRIEF SUMMARY

In some embodiments, a spinal fusion system may comprise an elongate, threaded, cylindrical body comprising a first arm and a second arm separated by a discontinuity, the arms extending substantially perpendicularly from and integrally connected to a first end of the cylindrical body. There may be an inner space between the first and second arms. There may also be a tool engagement feature on the cylindrical body and an expansion mechanism configured to spread the first and second arms at an area opposite the first end of the cylindrical body by causing mechanical, elastic deformation of the cylindrical body or the first and second arms.

In some embodiments, the discontinuity is a gap. The system may further comprise third and fourth arms extending substantially perpendicularly from and integrally connected to the first end of the cylindrical body. The inner space may be located between the first, second, third, and fourth arms. The expansion mechanism may be configured to spread the first, second, third, and fourth arms at an area opposite the first end of the cylindrical body by causing mechanical, elastic deformation of the cylindrical body or the first, second, third, and fourth arms. The tool engagement feature may be located at the first end of cylindrical body. The first end of the cylindrical body may comprise a frustoconical tip. The system may further comprise a frustoconical wedge having a first thread. The wedge may be disposed within the inner space. The first thread may be fitted within complimentary second threads formed on the arms. Some embodiments may further comprise an opening disposed opposite the first end of the cylindrical body and between the first and second arms. The expansion mechanism may comprise a tapered wedge having a posterior end sized and shaped to be advanced into the opening and an anterior end having a greater diameter than the diameter of the opening.

The tapered wedge may comprise a thread configured to engage with the first and second arms to advance or withdraw the wedge into the opening. Some embodiments may further comprise at least one supplemental fixation screw sized and shaped to fit in an opening in the first or second arm. The expansion mechanism may comprise a first plurality of detents defined by multiple pairs of landings extending from the first arm inwardly and laterally and a second plurality of detents defined by multiple pairs of landings extending from the second arm inwardly and laterally toward the first plurality of detents. The first and second pluralities of detents may be separated by the discontinuity. The embodiment may further comprise a slider disposed within the inner space of the cylindrical body. The slider may have a keel extending into at least one of the first plurality of detents and at least one of the second plurality of detents. The first plurality of detents may be arranged along a first longitude of the cylindrical body and the second plurality of detents may be arranged along a second longitude of the cylindrical body substantially opposite the first longitude.

The first or second plurality of detents may comprise a first detent having a first width and a second detent having a second width, wherein the first width is larger than the second width. The first or second plurality of detents may comprise a first pair of landings separated by a first distance and a second pair of landings separated by a second distance, wherein the first distance is larger than the second distance.

In some embodiments, a spinal fusion system may include an elongate, threaded, cylindrical body, having a first arm and a second arm separated by a discontinuity. The first and second arms may extend substantially perpendicularly from and be integrally connected to a first end of the cylindrical body. The system may further include an inner space between the first and second arms; a tool engagement feature; and an expansion mechanism configured to spread the first and second arms at an area opposite the first end by causing mechanical, elastic deformation of the cylindrical body. The expansion mechanism may comprise a cavity disposed between and defined by the first and second arms and a cam disposed within the cavity such that the cam spreads the first and second arms responsive to the cam rotating a first distance.

The spinal fusion system may have an elliptic cylinder shape. The spinal fusion system may include a one supplemental fixation screw sized and shaped to fit in an opening in the first or second arm. The cam may be disposed within the cavity in a first position and the cavity may include at least one detent configured to arrest the motion of the cam after the cam is rotated a pre-determined distance. The tool engagement feature may be located at the first end of cylindrical body. The first end of the cylindrical body may comprise a frustoconical tip.

In some embodiments, a method for fusing two vertebrae of the spine of a human or animal subject while imparting lordosis to a portion of the spine, may include inserting a fusion cage between the two vertebrae; spreading arms of the fusion cage by imparting rotational force to a cam disposed within a cavity of the fusion cage sufficient to cause elastic deformation of the fusion cage, thereby imparting lordosis to the portion of the spine.

In some embodiments, imparting rotational force to the cam comprises rotating the cam ¼ turn. Imparting rotational force to the cam may include rotating the cam until the cam is arrested by a detent. The method may further include implanting at least one supplemental fixation screw into at least one of the two vertebrae through an opening in the first or second arm.

BRIEF DESCRIPTION OF DRAWINGS

The accompanying drawings, which are incorporated into and constitute a part of the specification, illustrate embodiments of the disclosure and, together with the general description given above and the detailed description given below, serve to explain the principles of these embodiments.

DETAILED DESCRIPTION

Figure 1B:
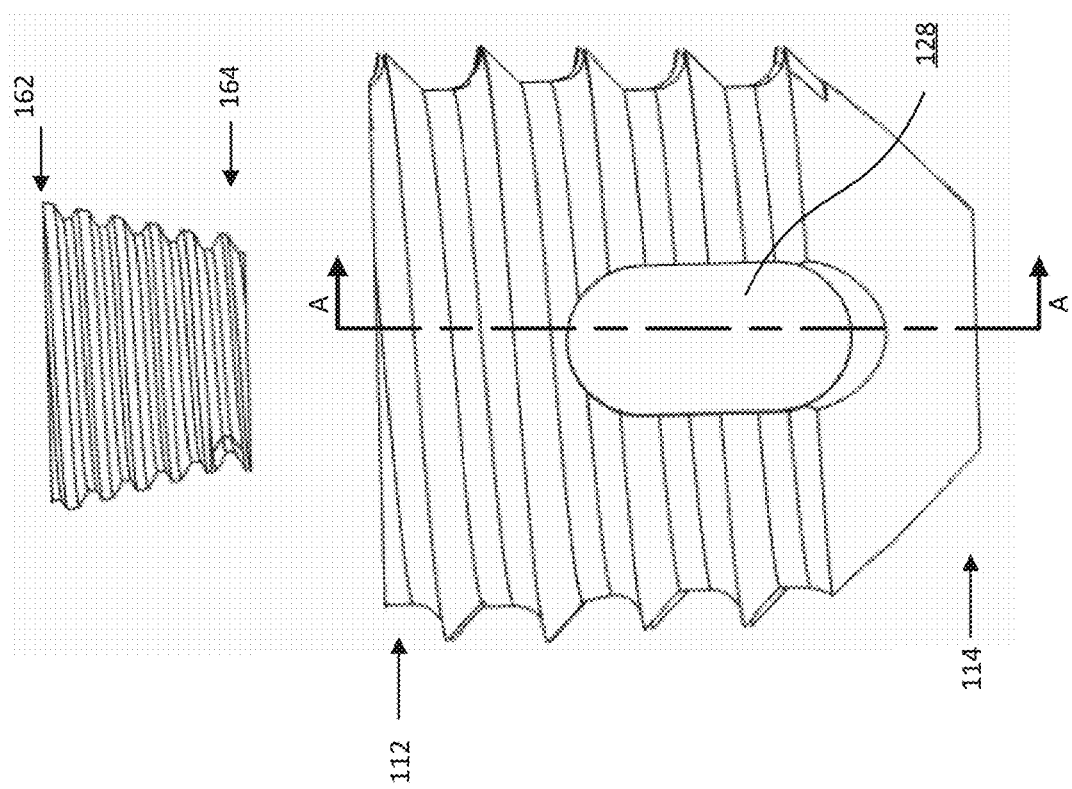
FIG. 1B illustrates a top view of the spinal fusion system of FIG. 1A

Disclosed embodiments generally relate to spinal fixation systems, methods, and devices that enable the addition of lordosis to a portion of the spine after the device is implanted. Embodiments may include lumbar, cervical, and other devices. The devices may be configured to have an end portion expand or spread apart. For example, one embodiment may be a cervical device configured to receive a threaded wedge in a cylindrical opening on the anterior end of the cage. As the wedge is advanced into the opening, the anterior portion of the cage elastically deforms, causing arms of the device to spread. In another embodiment, a lumbar device may include a movable component installed in the tip of the threaded cage. As the component is pushed anteriorly by an instrument the distal tip of the device spreads. In another example, a lumbar device may include an elliptic cylinder cam disposed within a cavity that may push against and expand arms of the device if the cam is rotated. In another embodiment, a lumbar device may include a rotatable wedge disposed within a space of the lumbar device. As the wedge is rotated, it travels through the space to expand a distal portion of the cage to increase lordosis by causing elastic deformation of the device. To facilitate the splitting or expansion of portions of the cage, the cage may include a discontinuity between sections of the cage to facilitate splitting of the device in a particular manner. References to top or bottom views of the embodiments disclosed herein may refer to the top or bottom of the embodiment as viewed when the embodiment is implanted in a spine.

FIGS. 1A-G illustrate one embodiment of a spinal fusion system 100. The system 100 may include a fusion cage 110 and a wedge 160. In some embodiments, the fusion cage 110 includes threads 116, a tool engagement feature 118, an inner space 120, a first arm 122, a second arm 124, a discontinuity 126, and openings 128, 130. In some embodiments, the wedge 160 may include threads 166, a tool engagement feature 168, an anterior end 162, and a posterior end 164.

The fusion cage 110 may include a substantially cylindrical shape defining an anterior end 112 and a posterior tip 114; however, other shapes and configurations are possible. As illustrated, the anterior end 112 is substantially flat, while the posterior tip 114 may have a frustoconical shape. In this manner, the fusion cage 110 may be generally bullet-shaped.

The threads 116 may be fixation structures disposed around a portion of the outer surface of the fusion cage 110. The threads 116 may enable improved engagement between the fusion cage 110 and the target surgical site, thus facilitating fixation. In some embodiments, the threads 116 may be configured to be self-tapping. In some embodiments, the threads may be configured to match with complimentary threads formed in a target surgical site (such as between discs in a cervical region of the spine). The threads 166 of the wedge 160 may be similarly configured to the threads 116 of the fusion cage 110. For example, the threads 166 may be configured to match with complimentary threads or other engagement features of the fusion cage 110 to facilitate driving the wedge into the inner space 120 of the fusion cage 110.

The tool engagement feature 118 may be a portion of the fusion cage 110 configured to engage or otherwise cooperate with a tool to facilitate the use of the fusion cage 110. For example, the tool engagement feature 118 may include means for connecting with guidance tools (e.g., to facilitate accurate placement of the fusion cage 110), insertion tools (e.g., for placing, inserting, or otherwise using the fusion cage 110), or other devices. The tool engagement feature 118 may take various shapes or forms, depending on the tool or tools that the tool engagement feature 118 is designed to interact with. For example, as illustrated, the tool engagement feature 118 includes an elongate slot designed to receive torque from a screw driver to facilitate placement and removal of the fusion cage 110. In other embodiments, however, other shapes and configurations of the tool engagement feature may be included.

Figure 1A:
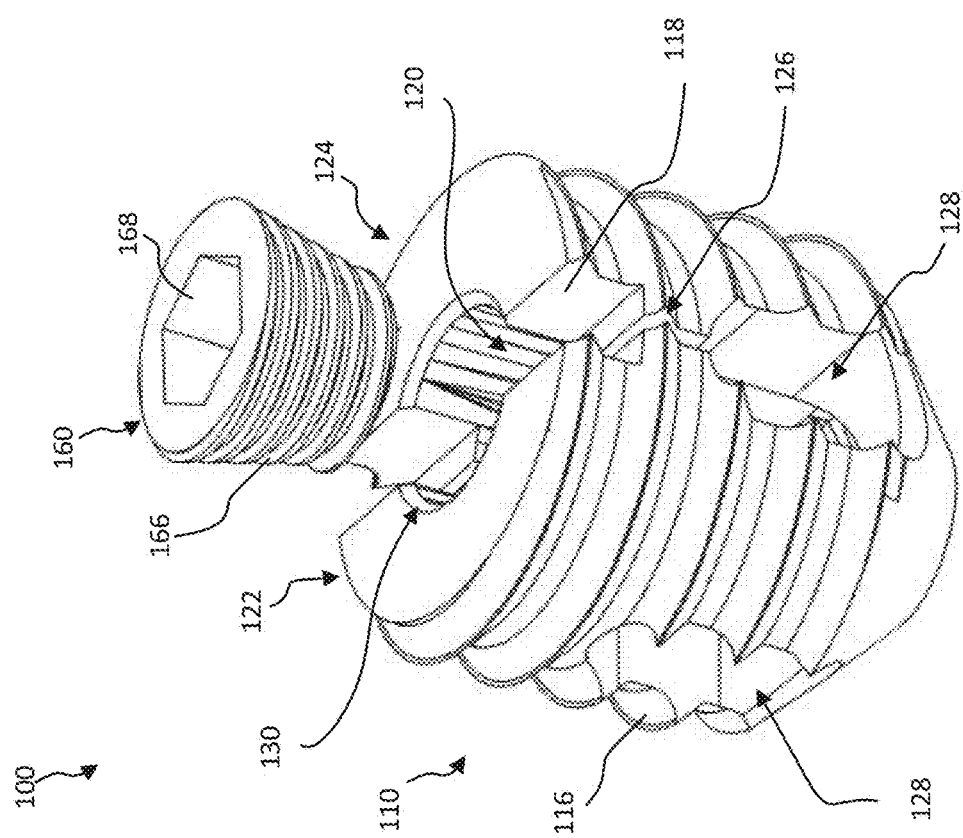
FIG. 1A illustrates a perspective view of a spinal fusion system.
Figure 1D:
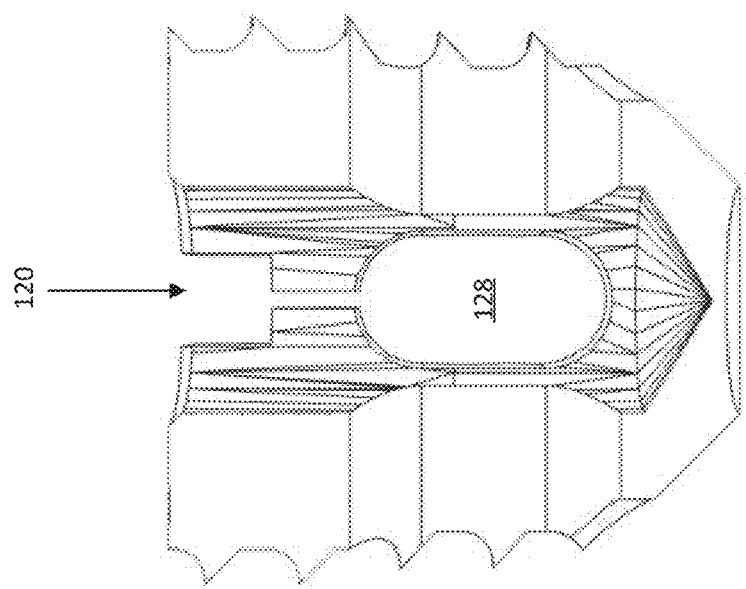
FIG. 1D illustrates a cutaway view of the spinal fusion system of FIG. 1A taken from the cutting line A-A of FIG. 1B.
Figure 1C:
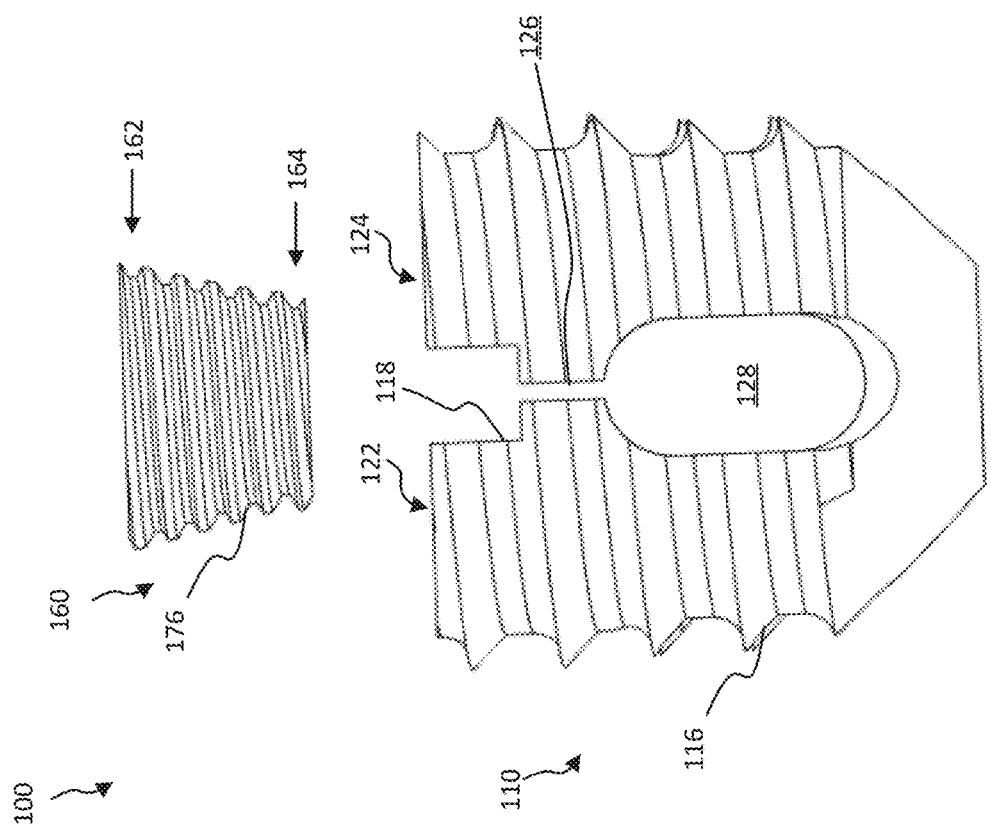
FIG. 1C illustrates a side view of the spinal fusion system of FIG. 1A substantially orthogonal to the top view of FIG. 1B.
Figure 1G:
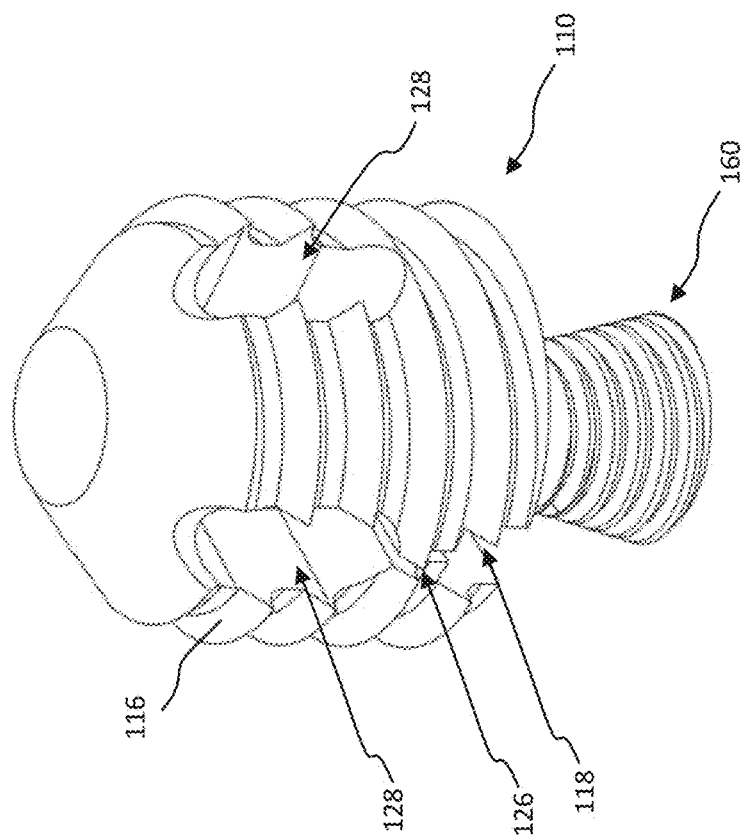
FIG. 1G illustrates a perspective view of the spinal fusion system of FIG. 1A.
Figure 1E:
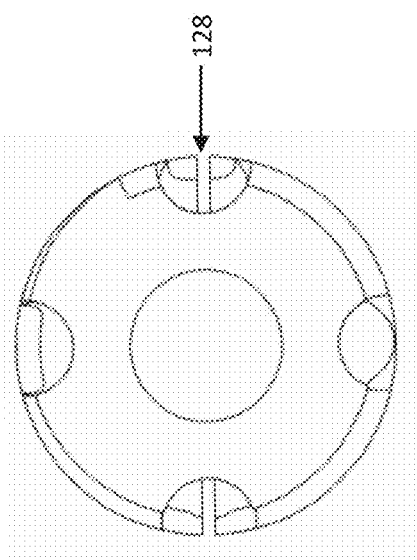
FIG. 1E illustrates a first end view of the spinal fusion system of FIG. 1A.
Figure 1F:
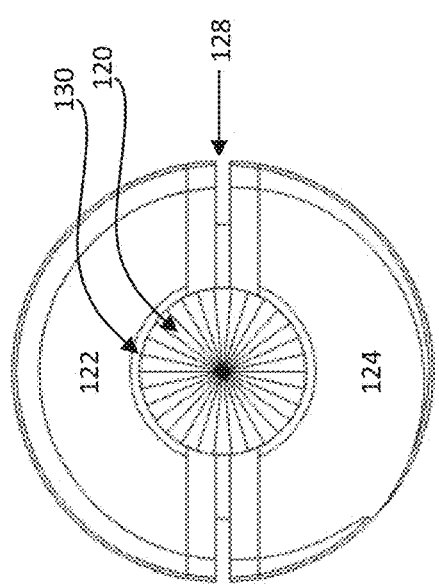
FIG. 1F illustrates a second end view of the spinal fusion system of FIG. 1A substantially opposite the first end view of FIG. 1E.

The inner space 120 may be an inner, hollow region of the fusion cage 110 defined in part by, for example, the first and second arms 122, 124. The inner space 120 may be configured to be filled with bone growth material to facilitate fusion. The inner space 120 may be sized or otherwise configured to receive at least a portion of the wedge 160. For example, as seen in FIG. 1D, the inner space 120 takes a substantially cylindrical shape, with a conical shape near the posterior of the fusion cage 110. The diameter of the inner space 120 may be generally smaller than the diameter of portions of the wedge 160, to facilitate spreading of the first and second arms 122, 124.

The first and second arms 122, 124 may be elongate sections of the fusion cage 110 that are separated by a discontinuity 126. The arms 122, 124 may be sections that extend substantially perpendicularly from a first end of the fusion cage 110. For example, as illustrated, the arms 122, 124 extend from the posterior tip 114; however, in some embodiments, the arms 122, 124 may be configured to extend from the anterior end 112. The arms 122, 124 may be configured to be spread apart, opposite of the end from which the arms 122, 124 extend. For example, if the arms extend from the posterior tip 114 of the fusion cage 110, then the arms 122, 124 may be configured to spread apart near the anterior end 112 of the fusion cage 110.

The portion of the fusion cage 110 from which the arms 122, 124 extend may be configured to elastically deform when the arms 122, 124 spread. This portion may include various components, shapes, or designs to encourage this deformation. This portion may or may not include a hinge or other component to promote expansion without deformation. For example, the spreading may be accomplished through deformation alone, through a combination of deformation and non-deforming expansion, and non-deforming expansion alone.

The discontinuity 126 may be a gap defined by the first and second arms 122, 124 or a region of different material configured to preferentially split or deform, enabling the separation of the first and second arms 122, 124. For example, in some embodiments, the discontinuity 126 may include a region of highly elastic or otherwise deformable material configured to accommodate the spreading of the arms 122, 124. The discontinuity 126 may, but need not be, a continuous region and may be incorporated into different features of the cage 110. For example, as illustrated in FIG. 1A, the discontinuity 126 between the first and second arms 122, 124 is defined, in part, by the space formed by the inner space 120, the openings 128, and the tool engagement feature 118; and the discontinuity 126 extends around three sides of the fusion cage 110, from the opening 128, through the tool engagement feature 118, the opening 130, another end of the tool engagement feature 118, and another opening 128.

Figure 2A:
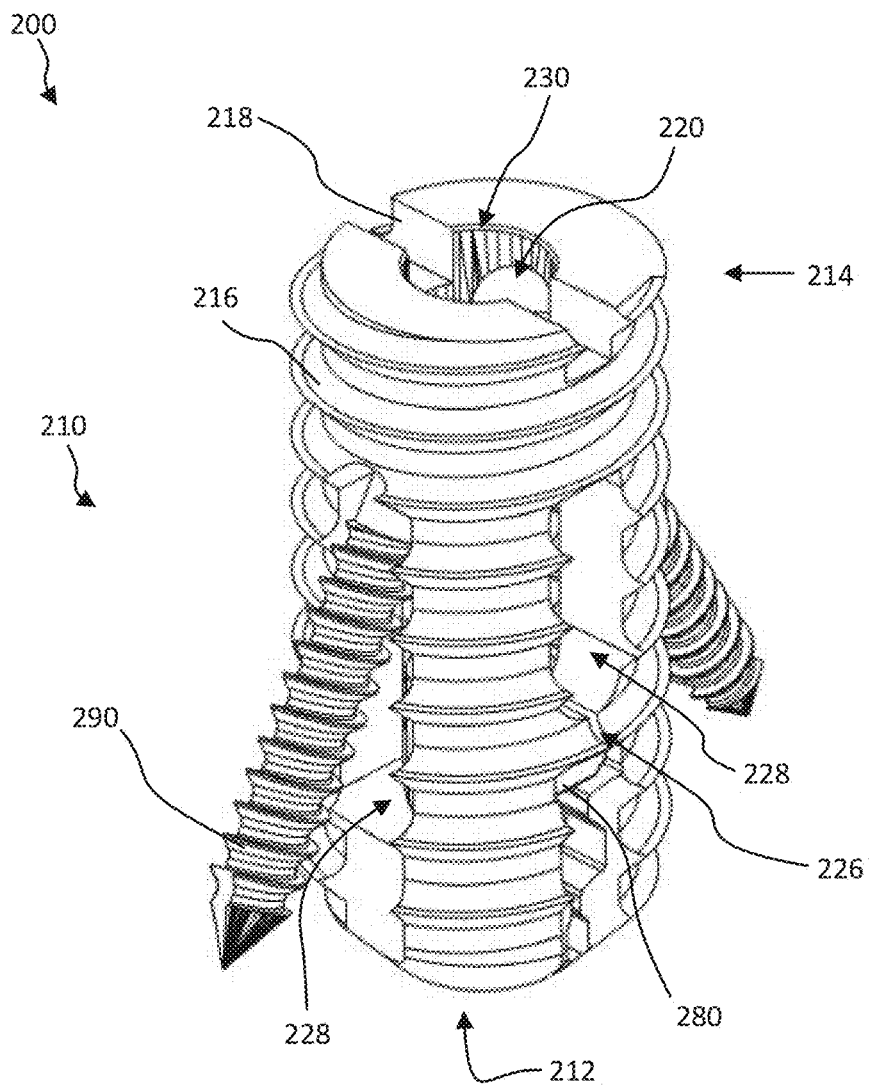
FIG. 2A illustrates a perspective view of a spinal fusion system according to some embodiments.
Figure 2B:
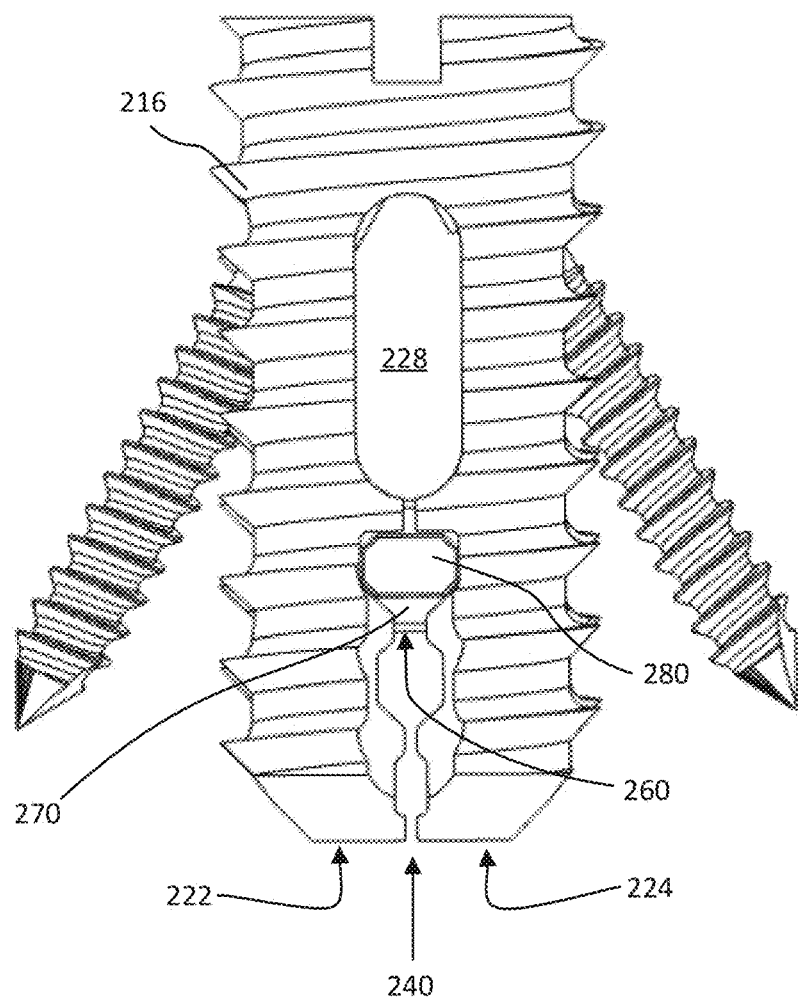
FIG. 2B illustrates a side view of the spinal fusion system of FIG. 2A.

The openings 128, 130 may be regions linking the inner space 120 of the fusion cage 110 with an area outside of the fusion cage 110. As illustrated, there are five openings 128 in the fusion cage 110; four openings 128 are defined on an outer diameter of the fusion cage 110 and another opening 130 is located on the anterior end 112 of the fusion cage 110. The openings 128 may be configured to encourage bone growth in order to improve the fixation of the fusion cage 110 with the spine. In some embodiments, the openings 128, 130 may be configured to receive a screw to improve fixation (e.g., similar to the screw placement in FIG. 2A). The openings 128, 130 may be configured to be in communication with the inner space 120.

The opening 130 may be configured to receive the wedge 160. For example, the opening 130 may be sized to accommodate a portion (e.g., the posterior end 164) of the wedge 160 without deformation of the fusion cage 110. The opening 130 may be sized to accommodate the wedge 160 without deformation of the fusion cage 110 for a particular distance of advancement (e.g., a distance sufficient for a user to be able to tell that the wedge 160 is properly seated in the opening), but then, after a further distance, the opening 130 cannot further accommodate the wedge 160 without deformation. The thread design of the wedge 160 and fusion cage 110 interface may be chosen such that the components cannot loosen on their own. In some embodiments, the sizing of the threading may be chosen to fit with the larger end of the wedge 160. Continued advancement of the wedge 160 then causes elastic deformation of the fusion cage 110 and spreading of the arms 122, 124.

The wedge 160 may have a substantially frustoconical shape. For example, the anterior end 162 may have a smaller diameter than the posterior end 164. The diameter of the posterior end 164 may correlate to a maximum-desired spread distance of the arms 122, 124 when the wedge 160 is fully advanced into the fusion cage 110. What constitutes full advancement of the wedge 160 into the fusion cage 110 may vary depending on the configuration of the system 100. In various embodiments, for example, full advancement may involve advancing the wedge 160 completely within the inner space 120, advancing the wedge 160 until the wedge 160 is flush with an outer surface of the fusion cage, or advancing the wedge 160 but leaving a portion of the wedge 160 outside of the fusion cage 110. The tool engagement feature 168 may be configured to receive the distal end of a tool and transmit rotational (or other) force from the tool to cause the wedge to advance. The tool engagement feature 168 may have similar properties as the tool engagement feature 118 of the fusion cage 110. As illustrated, the tool engagement feature 118 has a substantially hexagonal shape, but other configurations of the tool engagement feature 118 may be used.

FIGS. 2A-G illustrate another embodiment of a spinal fusion system 200, including a fusion cage 210, a slider 260, and screws 290. In some embodiments, the fusion cage 210 includes an anterior end 212, a posterior end 214, threads 216, a tool engagement feature 218, an inner space 220, a first arm 222, a second arm 224, a discontinuity 226, openings 228, 230, and an expansion mechanism 240. In some embodiments, the slider 260 (which may be seen more clearly in FIGS. 2H-J) may include a slider core 270 and a slider keel 280.

In some embodiments, the fusion cage 210 may have a substantial number of similarities to the fusion cage 110, and the component regions may also be similar, including but not limited to the threads 116, 216, the tool engagement features 118, 218, the inner spaces 120, 220, the first arms 122, 222, the second arms 124, 224, the discontinuities 126, 226, the openings 128, 228, 130, 230, and other features. The systems 100, 200 may have differences as well.

For example, in the illustrated embodiment, the fusion cage 210 is configured such that the end that separates is the end opposite the tool engagement feature 218. Specifically, the tool engagement feature 218 is located on the posterior end of the fusion cage 210, while the arms 222, 224 are configured to spread at the anterior end 212 of the fusion cage.

Like the discontinuity 126, the discontinuity 226 separates the arms 222, 224 of the fusion cage 210. However, as illustrated, unlike the discontinuity 126, the discontinuity 226 extends through the openings 228, but not through the tool engagement feature 218.

The expansion mechanism 240 may be a region of the fusion cage 210 configured to spread the arms 222, 224 of the device. The expansion mechanism 240 may encompass portions of the arms 222, 224 and regions between the arms 222, 224. For example, in certain embodiments, the arms 222, 224 may include multiple pairs of landings 242, 244, 246, 248 that are a part of the expansion mechanism 240. As illustrated, the pairs of landings 242, 244, 246, 248 extend from the arms 222, 242 inwardly and laterally towards each other but are separated by the discontinuity 226. The pairs of landings 242, 244, 246, 248 and the arms 222, 224 may define multiple detents 250, 252, 254. The detents 250, 252, 254 may be regions where the slider keel 280 may be received and rest. The landings 242, 244, 246, 248 may have an angled feature (such as a side) against which the slider keel 260 may be pushed and slide.

Figure 2C:
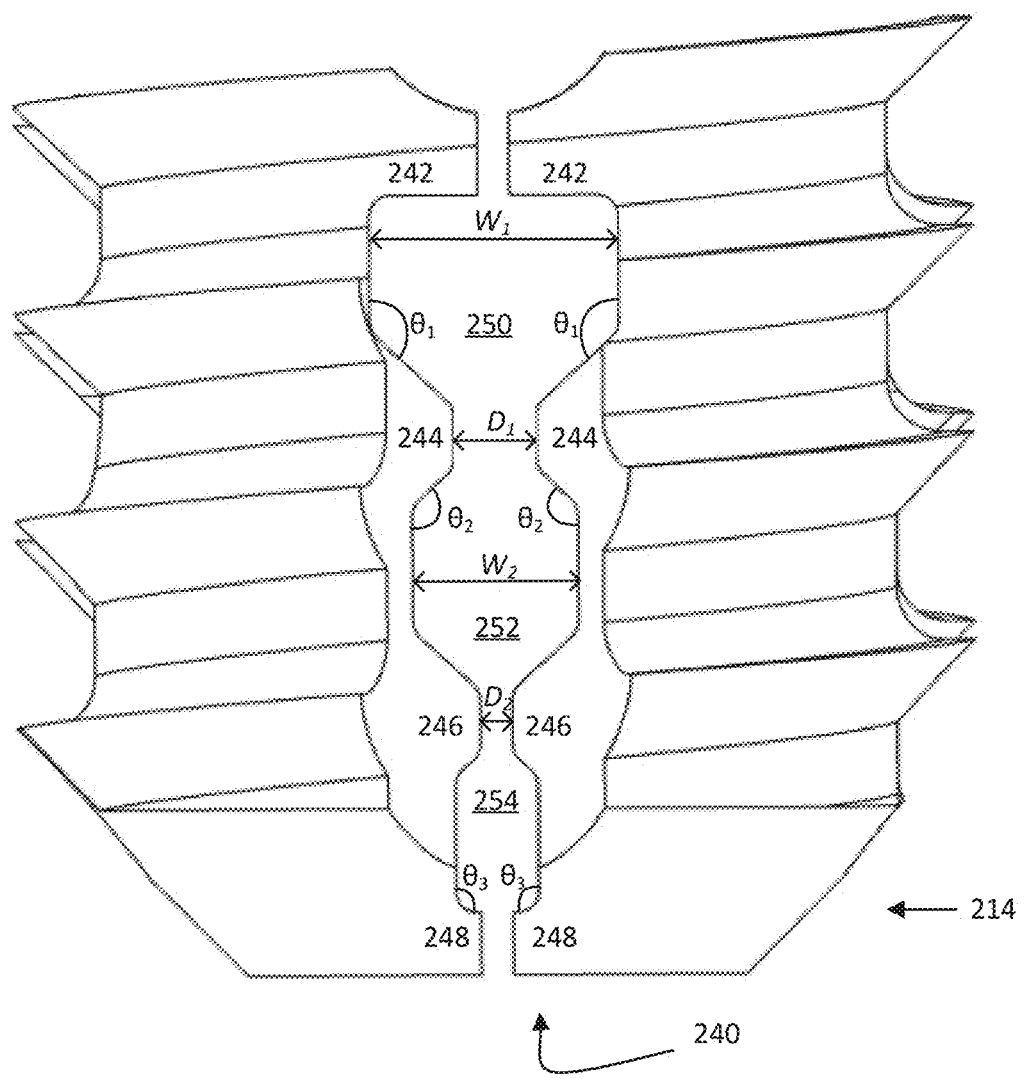
FIG. 2C illustrates an enlarged view of the expansion mechanism illustrated in FIG. 2B.
Figure 2D:
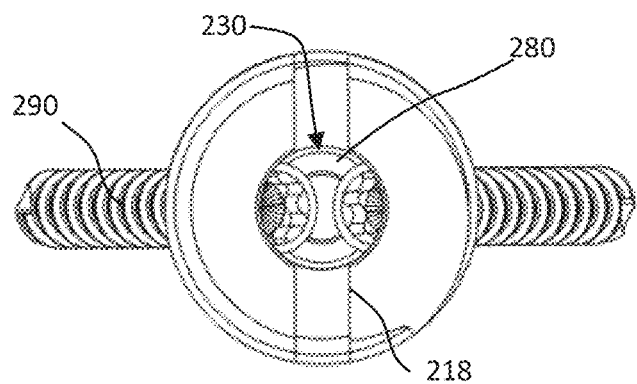
FIG. 2D illustrates a first end view of the spinal fusion system of FIG. 2A.
Figure 2E:
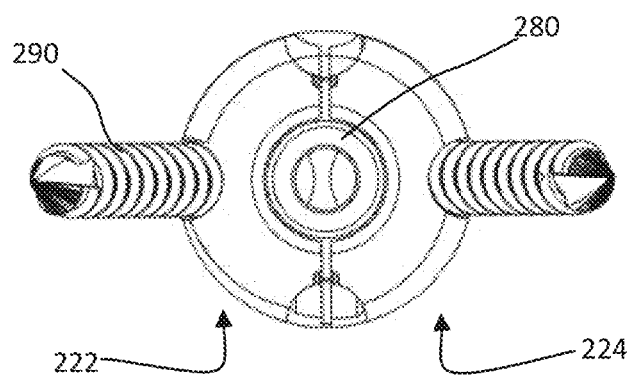
FIG. 2E illustrates a second end view of the spinal fusion system of FIG. 2A substantially opposite the first end view of FIG. 2D.
Figure 2G:
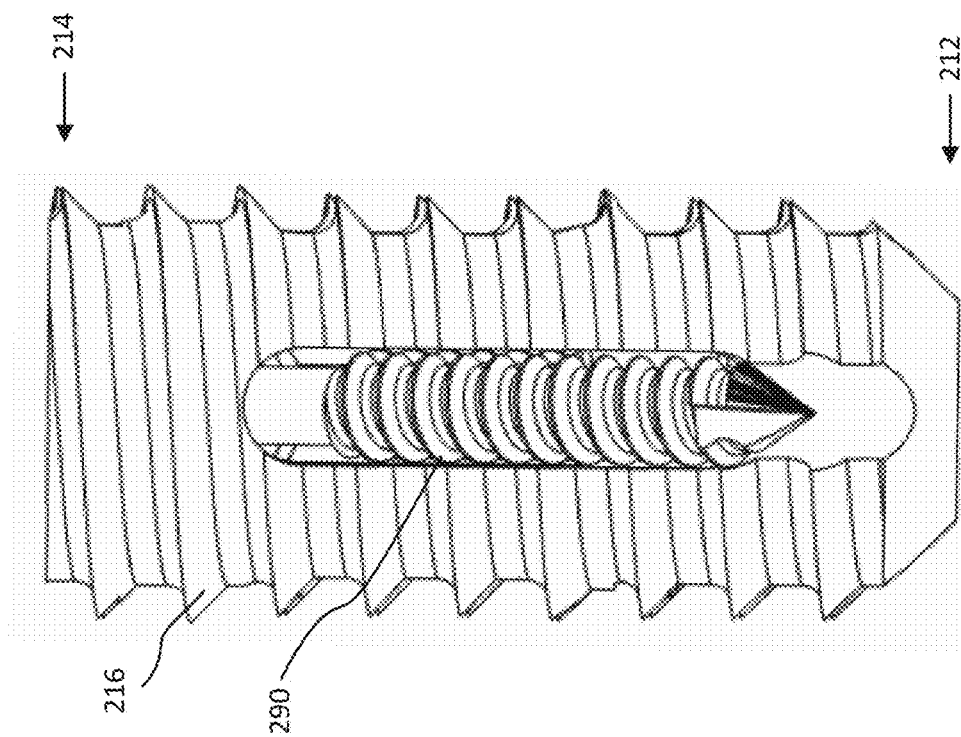
FIG. 2G illustrates a top view of the spinal fusion system of FIG. 2A.
Figure 2F:
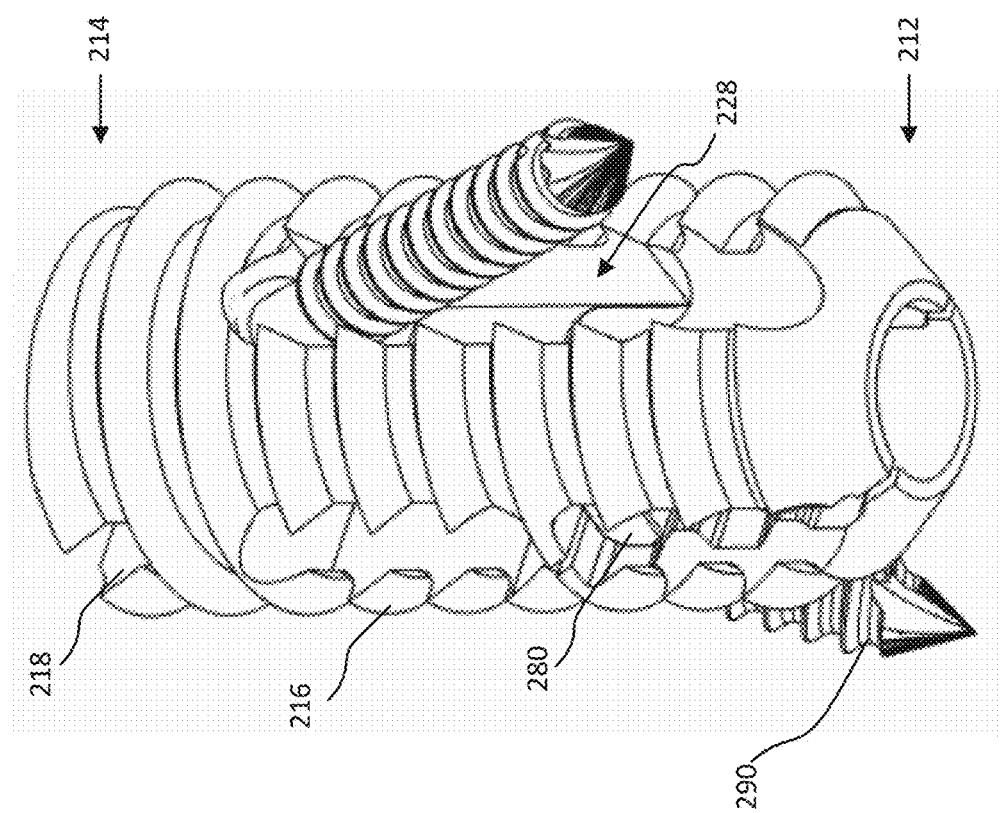
FIG. 2F illustrates a perspective view of the spinal fusion system of FIG. 2A.

With reference to FIG. 2C, the landings 242, 244, 246, 248 extend from the arms 222, 224 and take the form of trapezoidal prisms. For example, the posterior-most side of the landings 242 extends at an angle $\theta_1$ from the walls of the detent 248, while the anterior-most side of the landings 242 extends at an angle $\theta_2$ from the lateral walls of the detent 250.

In certain embodiments, expansion mechanism 240 may be configured to spread or contract the arms 222, 224 when a user imparts force on the slider keel 260. For example, the user may push the slider 260 anteriorly while the slider keel 280 rests within the detent 250. As the slider 260 is moved anteriorly, the keel 280 encounters the landing 244. The angle $\theta_1$ at which the landing 244 extends from the arms 222, 224 causes some of the force on the keel 280 to become lateral force. The lateral force may cause spreading of the arms 222, 224. After the arms 222, 224 have spread enough to allow passage of the keel 280 through the pair of landings 244, the keel 280 may arrive at and become lodged in detent 252. As illustrated, the width $w_2$ of the detent 252 is smaller than the width $w_1$ of the detent 250 and is smaller than the width of the keel 280. As a result, when the keel 280 rests within the detent 520, the arms 222, 224 are maintained in a slightly spread configuration. The keel 280 may then be moved again to a smaller detent (e.g., from the detent 252 to the detent 254) in order to further the spread of the arms 222, 224. A similar process may be used to decrease the spread of the arms 222, 224 by moving the slider 260 posteriorly into detents having a larger width.

The angles of the landings 242, 244, 246, 248 may be configured to encourage or discourage movement of the slider 260 between the detents 250, 252, 254. For example, as $\theta_1$ approaches 180°, less force is required to push the slider 260 from the detent 248 to the detent 250. As another example, as illustrated, $\theta_3$ is a substantially right angle. This may prevent the keel 280 from moving anteriorly out of the detent 254. As another example, the landing 242 extends at a substantially right angle to resist posterior movement of the keel 280. The angles may be selected based on the spread of the arms 222, 224. For example, when the keel 280 is located within detent 254, the arms 222, 224 may be spread sufficiently far to change the effective angle of the landing 248.

In some embodiments, the spacing between landings within a pair of landings may vary across pairs of landings. For example, the space between the pair of landings 244 is a distance $D_1$ and the distance between the pair of landings 246 is distance $D_2$. In the unexpanded configuration, the distance $D_2$ is smaller than the distance $D_1$. The distance may be selected to increase or decrease the relative ease (e.g., the amount of force) at which the keel 280 may be moved from one detent to another. For example, a larger distance may result in comparatively easier movement of the keel 280 than a smaller distance. In some embodiments, the distance is selected to account for the expansion of the arms 222, 224. For example, as the distance between the arms 222, 224 increases as the arms 222, 224 are spread, so too will the distance between the landings within a pair of landings. Accordingly, in some embodiments, the un-spread distance between the landings may be selected based on the distance that will result once the arms 222, 224 are spread. For example, the un-spread distance between landings may be smaller in pairs closer to an end of the arms 222, 224.

While the expansion mechanism 240 is illustrated as being uniform on both sides of the fusion cage 210, it need not be. For example, in some embodiments, it may be desirable to have non-uniform spreading of the arms 222, 224. Accordingly, the expansion mechanism 240 on one side of the fusion cage 210 may be different from the expansion mechanism on the other side of the fusion cage 210. For example, the detents of one of the expansion mechanisms 240 may be different from the opposite expansion mechanism (e.g., by having a different shape, location, or other features). This configuration may promote asymmetric expansion, which may be advantageous in certain circumstances.

In some embodiments, the expansion mechanism 240 may be configured to use a threaded component (e.g., wedge 160, a screw, or a nut) instead of or in addition to the slider 260 to expand the arms 222, 224. For example, a threaded wedge or screw may drive a slider into a detent. As another example, the expansion mechanism 240 may be configured similarly to the wedge-and-opening mechanism of fusion cage 110. The expansion mechanism 240 may include an opening configured to receive a wedge without deformation of the fusion cage 210 for a particular distance of advancement, but then, after the opening cannot further accommodate the wedge 160 without deformation, the fusion cage 210 deforms. Continued advancement of the wedge then causes elastic deformation of the fusion cage 210 and the spreading of the arms 222, 224. The wedge may be located within the inner space 220, such that a user inserts a tool through the opening 230 to engage a tool engagement feature of the wedge to impart rotational force to the wedge.

Figure 2H:
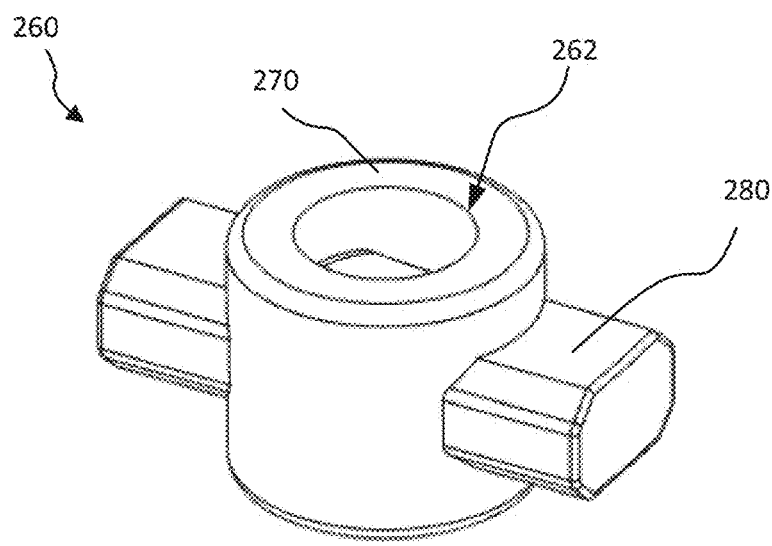
FIG. 2H illustrates a perspective view of a slider according to some embodiments.
Figure 2I:
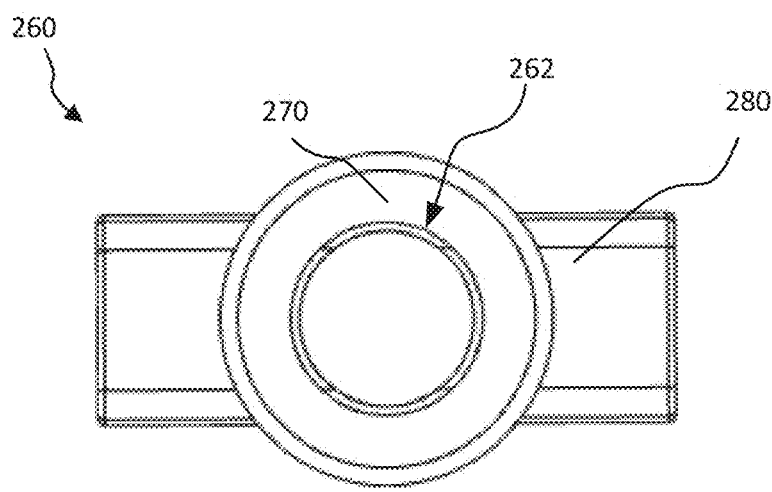
FIG. 2I illustrates an end view of the slider of FIG. 2H.
Figure 2J:
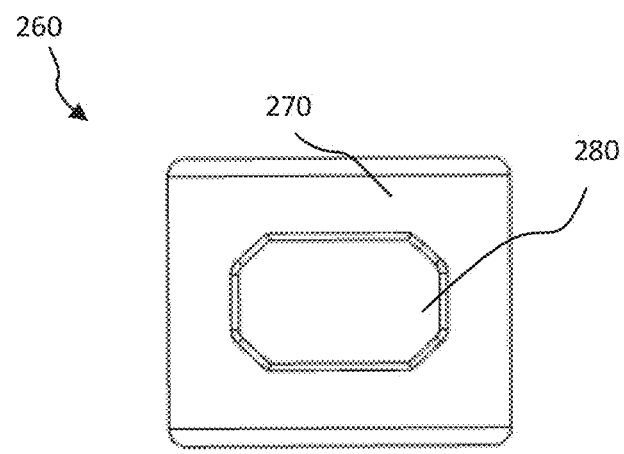
FIG. 2J illustrates a side view of the slider of FIG. 2H.

FIGS. 2H-J illustrate the slider 260 in isolation, according to certain embodiments. As illustrated, the slider core 270 is a substantially cylindrical element, and the slider keel 280 is an elongate, rectangular element extending perpendicularly through the slider core 270. There is an opening 262 extending through both the slider core 270 and the slider keel 280. The opening 262 may be configured to interface with an instrument inserted through the opening 230. The slider core 270 and keel 280 may be integrally formed or may be separate components. For example, in some embodiments, the slider core 270 includes an opening through which the slider keel 280 may be inserted. This configuration may aid in manufacturing or use of the system 200. For example, the slider core 270 may be inserted through the opening 230 of the fusion cage 210 and into the inner space 220. The core 270 may then be moved into a position aligning with a desired detent 250, 252, 254 and the keel 280 may be inserted to substantially fix the slider 260 in position. The slider 260 may be configured to receive expansion and/or contraction energy from an instrument.

The slider core 270 may be sized and shaped to slide within the opening 230 and the inner space 220. The mechanical fit between the outer surface of the slider core 270 and the inner surface of the inner space 220 may vary depending on desired applications and uses. For example, a tighter fit may result in decreased play or binding as the slider 260 moves through the inner space 220.

As illustrated, the slider keel 280 has chamfered edges. These edges may improve the pushability of the keel 280 between detents 250, 252, 254 within the expansion mechanism 240. Other configurations, however, are also possible to encourage or discourage movement of the slider 260 within the expansion mechanism. For example, the keel 280 may have triangular or other profiles.

FIGS. 3A-I illustrate an embodiment of a spinal fusion system 300, including a fusion cage 310 and a cam 360. In certain embodiments, the fusion cage 310 includes an anterior end 312, a posterior end 314, threads 316, a tool engagement feature 318, an inner space 320, a first arm 322, a second arm 324, a discontinuity 326, openings 328, 330, and an expansion mechanism 340. In some embodiments, the cam 360 (which may be seen more clearly in FIGS. 3G-I) may include a tool engagement feature 378.

In some embodiments, the fusion cage 310 may be substantially similar to the fusion cage 210 and the features may also be similar, including but not limited to the threads 216, 316, the tool engagement features 218, 318, the inner spaces 220, 320, the first arms 222, 322, the second arms 224, 324, the discontinuities 226, 326, the openings 228, 328, 230, 330, and other features. In addition, the illustrated embodiment of the fusion cage 310 has the tool engagement feature 318 located on the posterior end 314 and has the arms 322, 324 configured to spread near the anterior end 312. The systems 200, 300 have differences as well.

Figure 3A:
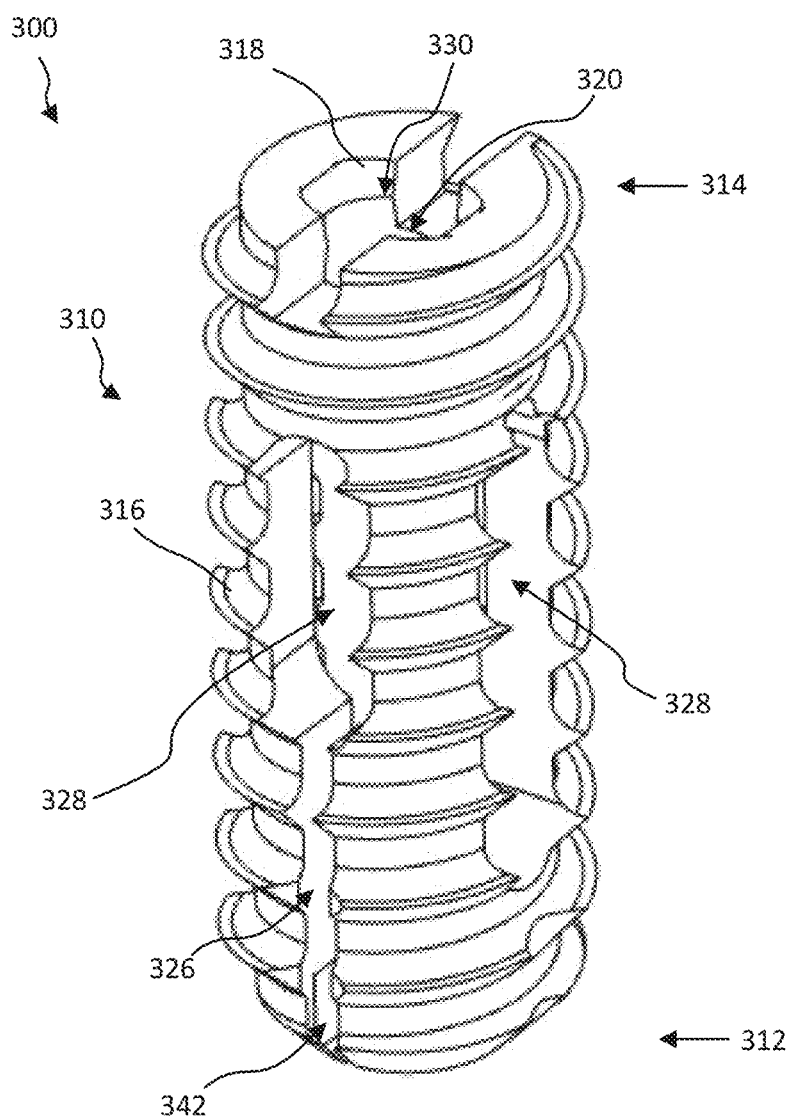
FIG. 3A illustrates a perspective view of a spinal fusion system according to some embodiments.
Figure 3B:
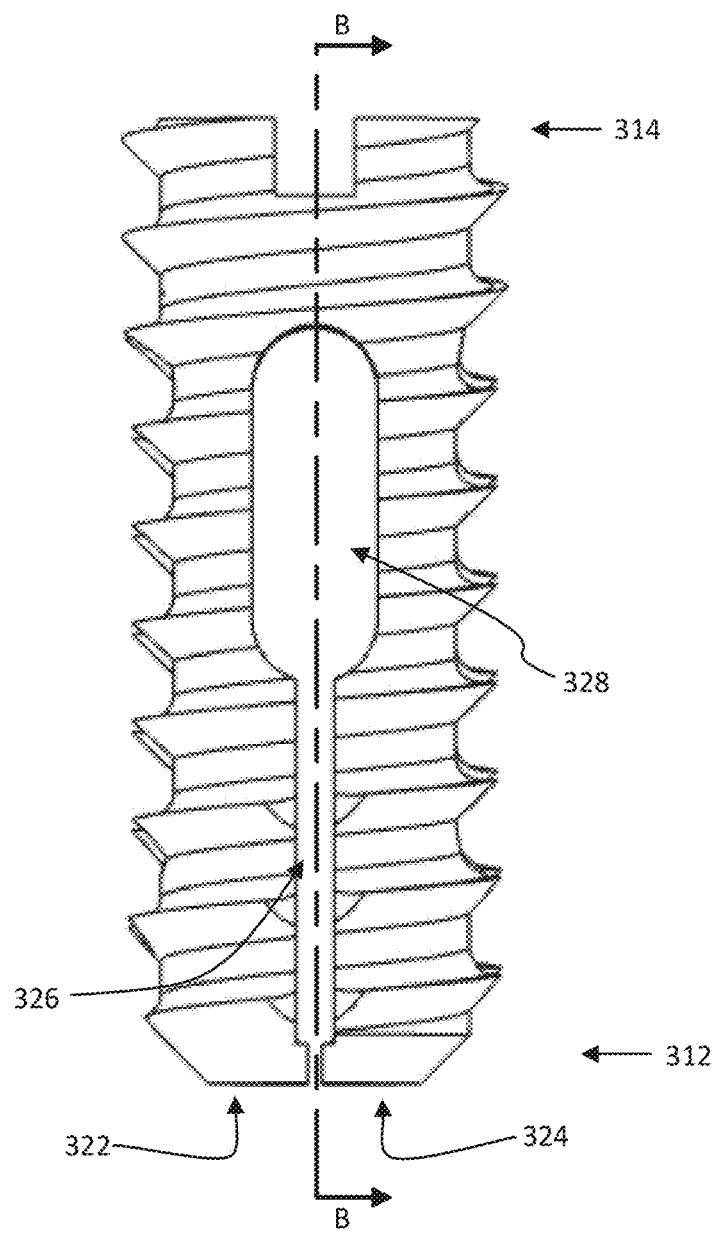
FIG. 3B illustrates a side view of the spinal fusion system of FIG. 3A.
Figure 3D:
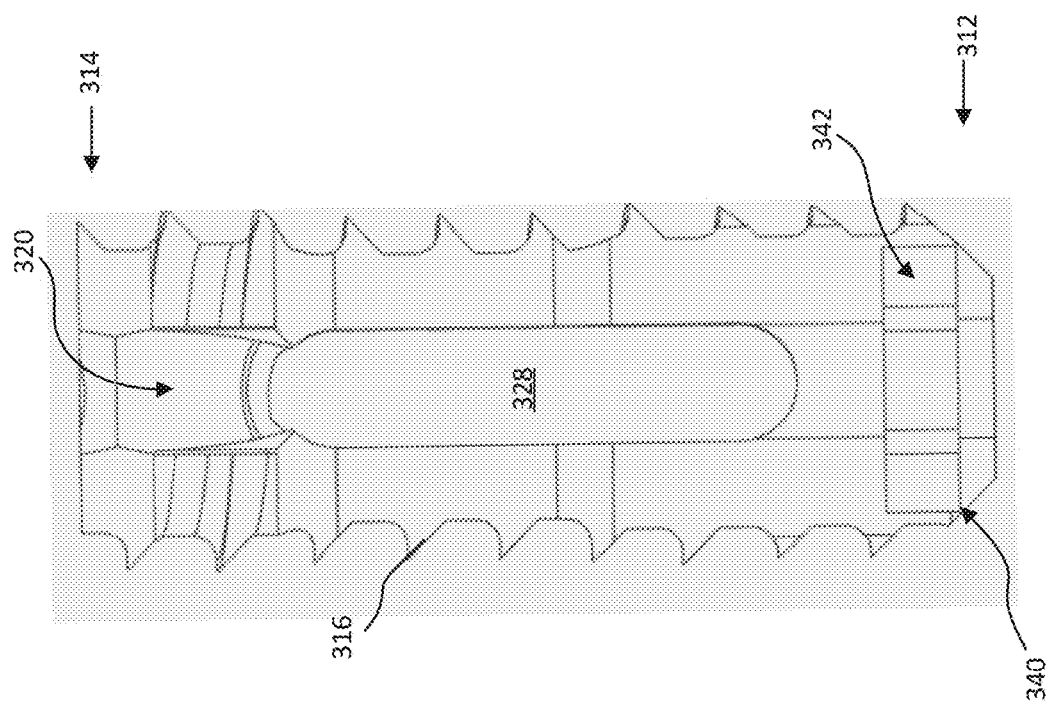
FIG. 3D illustrates a cutaway view of the spinal fusion system of FIG. 3A taken from the cutting line B-B of FIG. 3B.
Figure 3C:
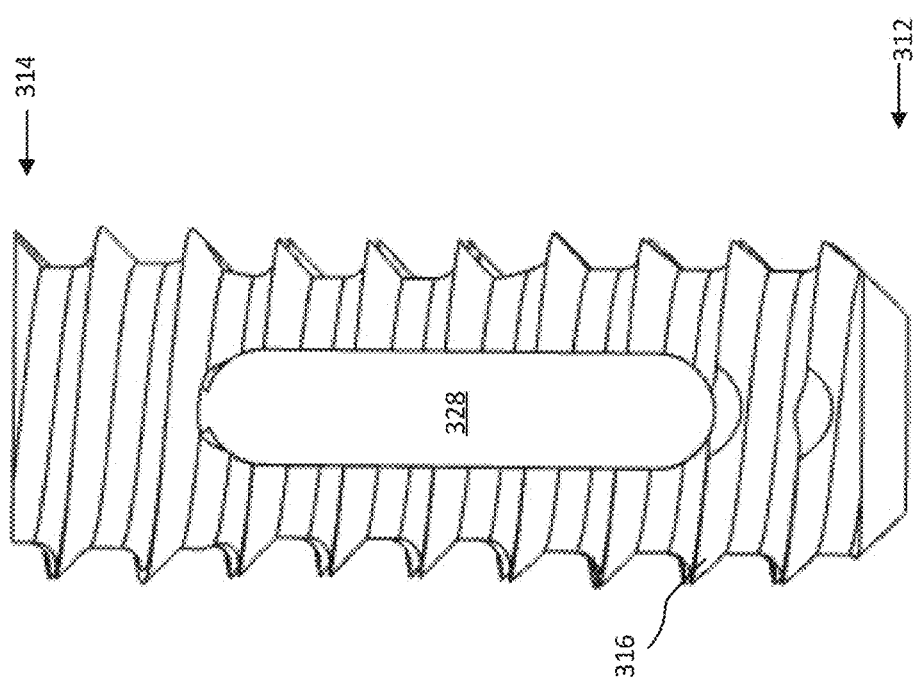
FIG. 3C illustrates a top view of the spinal fusion system of FIG. 3A and is substantially orthogonal to the side view of FIG. 3B.
Figure 3F:
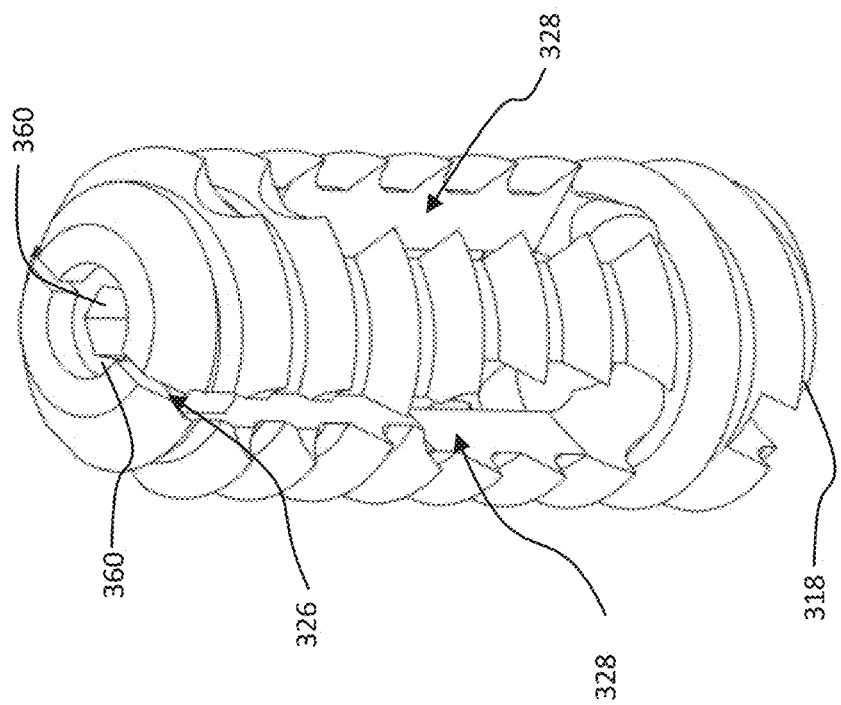
FIG. 3F illustrates a second end view of the spinal fusion system of FIG. 3A, including a cam.
Figure 3E:
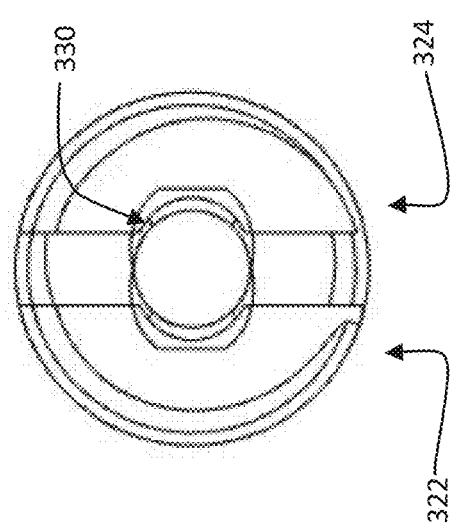
FIG. 3E illustrates a first end view of the spinal fusion system of FIG. 3A.
Figure 3G:
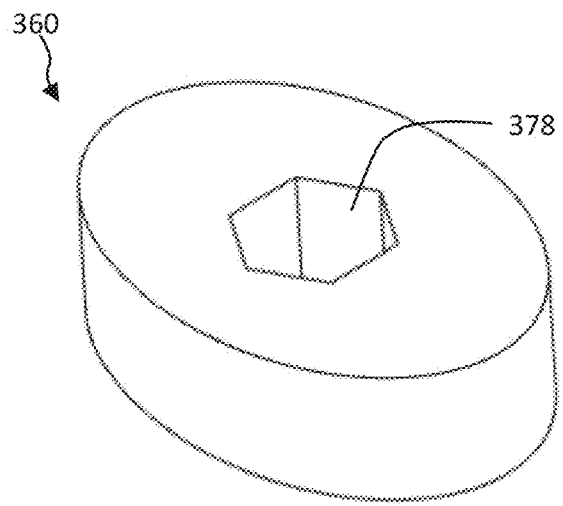
FIG. 3G illustrates a perspective view of a cam.
Figure 3H:
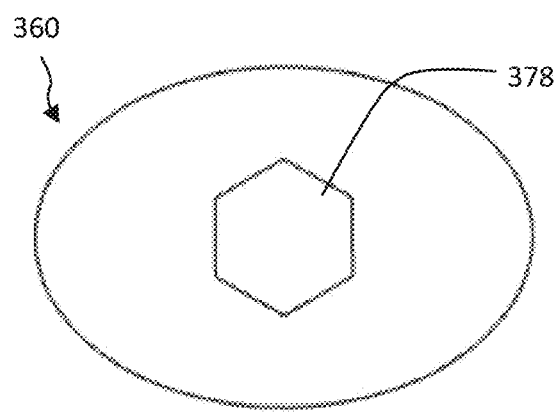
FIG. 3H illustrates an end view of the cam of FIG. 3G.
Figure 3I:
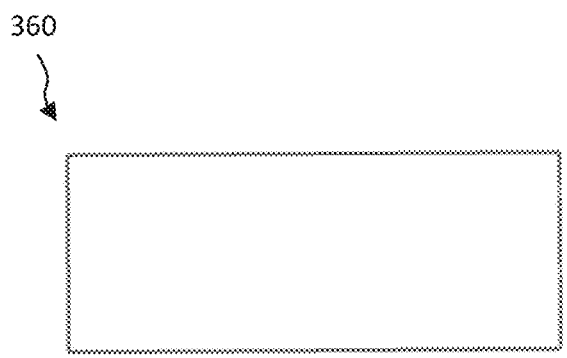
FIG. 3I illustrates a side view of the cam of FIG. 3G.

The expansion mechanism 340 of the system 300 is different from the expansion mechanism 240 of the system 200. For example, while the expansion mechanism 240 uses a keel-and-detent system for expansion, the expansion mechanism 340 uses a rotating cam 360. Specifically, as can be seen in FIG. 3D, the fusion cage 310 and the arms 322, 324 define a cavity 342 near the anterior end 312 of the fusion cage 310, in which a cam 360 may be disposed. The cavity 342 may be sized, shaped, or otherwise configured so that the cam 360 may be disposed within it. The cavity 342 may be shaped such that there is a tight mechanical fit between the outer wall of the cam 360 and the cavity 342. Spreading of the arms 322, 324 may be cause by rotating the cam 360. For example, in some embodiments, the cam 360 is elongate and has a tight fit within the cavity 342. The force of rotation imparted by the tool causes the arms 322, 324 to spread to accommodate the rotation of the cam 360. In some embodiments, the cavity 342 may include a detent or other feature in order to arrest the motion of the cam 360 once the cam 360 has been rotated a particular distance.

The cam 360 (which may be best seen in FIGS. 3G-3I) may be a substantially elliptic cylinder. There may be a tool engagement feature 378 disposed on a surface of the cam 360 so that the cam may be rotated through the use of a tool.

FIGS. 4A-H illustrate an embodiment of a spinal fusion system 400, including a fusion cage 410 and a wedge 460. In certain embodiments, the fusion cage 410 includes an anterior end 412, a posterior end 414, threads 416, a tool engagement feature 418, a first arm 421, a second arm 422, a third arm 423, and a fourth arm 424, discontinuities 426, 427, openings 428, 430, and an expansion mechanism 440. The expansion mechanism 440 may be located at an end of the fusion cage 410 (e.g., the posterior end 414, as illustrated). In some embodiments, the wedge 460 (which may be seen more clearly in FIGS. 4E-4H) may include an anterior end 462, a posterior end 464, a thread 466, and a tool engagement feature 468. The wedge 460 may have a frustoconical shape.

Figure 4A:
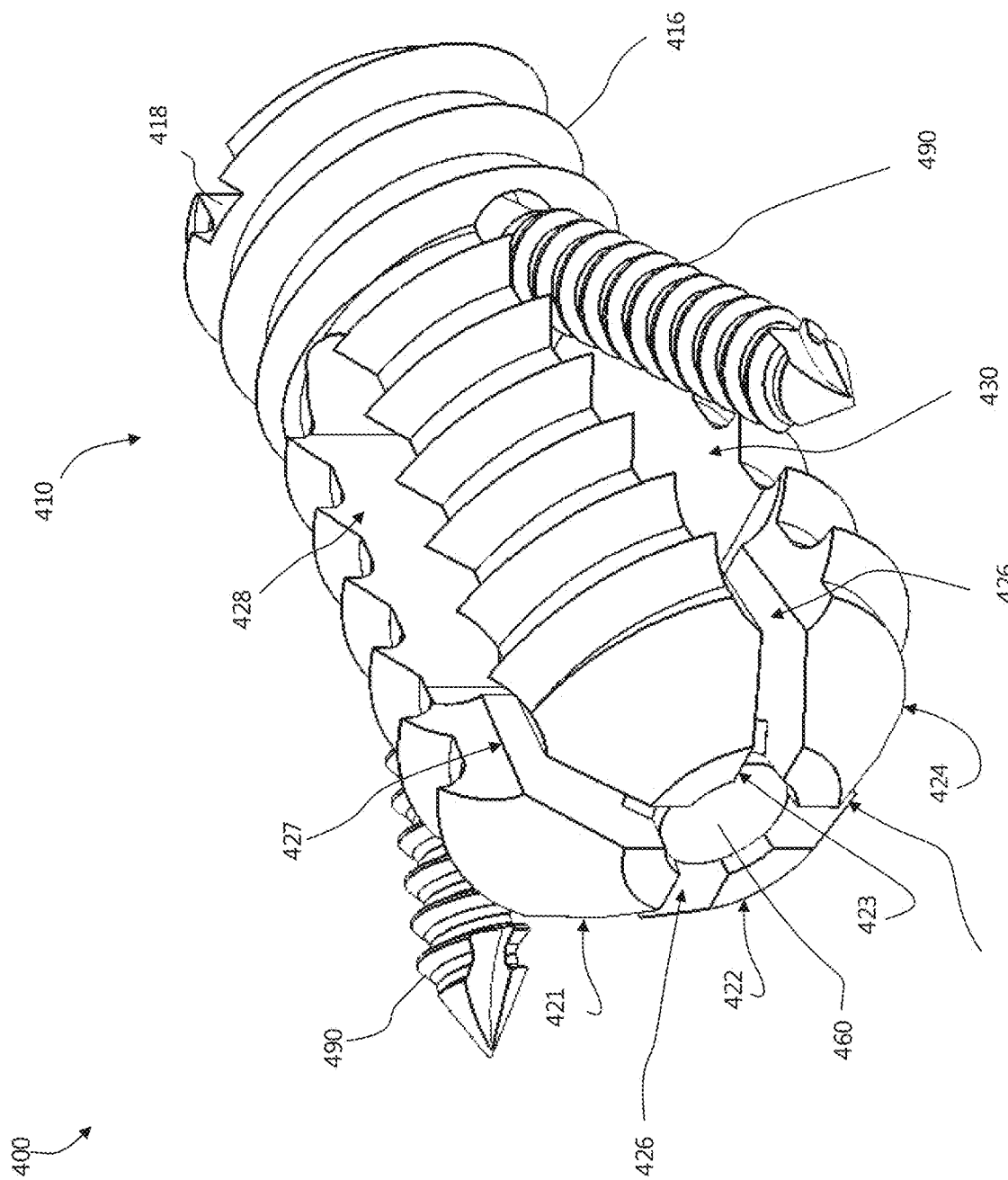
FIG. 4A illustrates a perspective view of a spinal fusion system according to some embodiments.
Figure 4B:
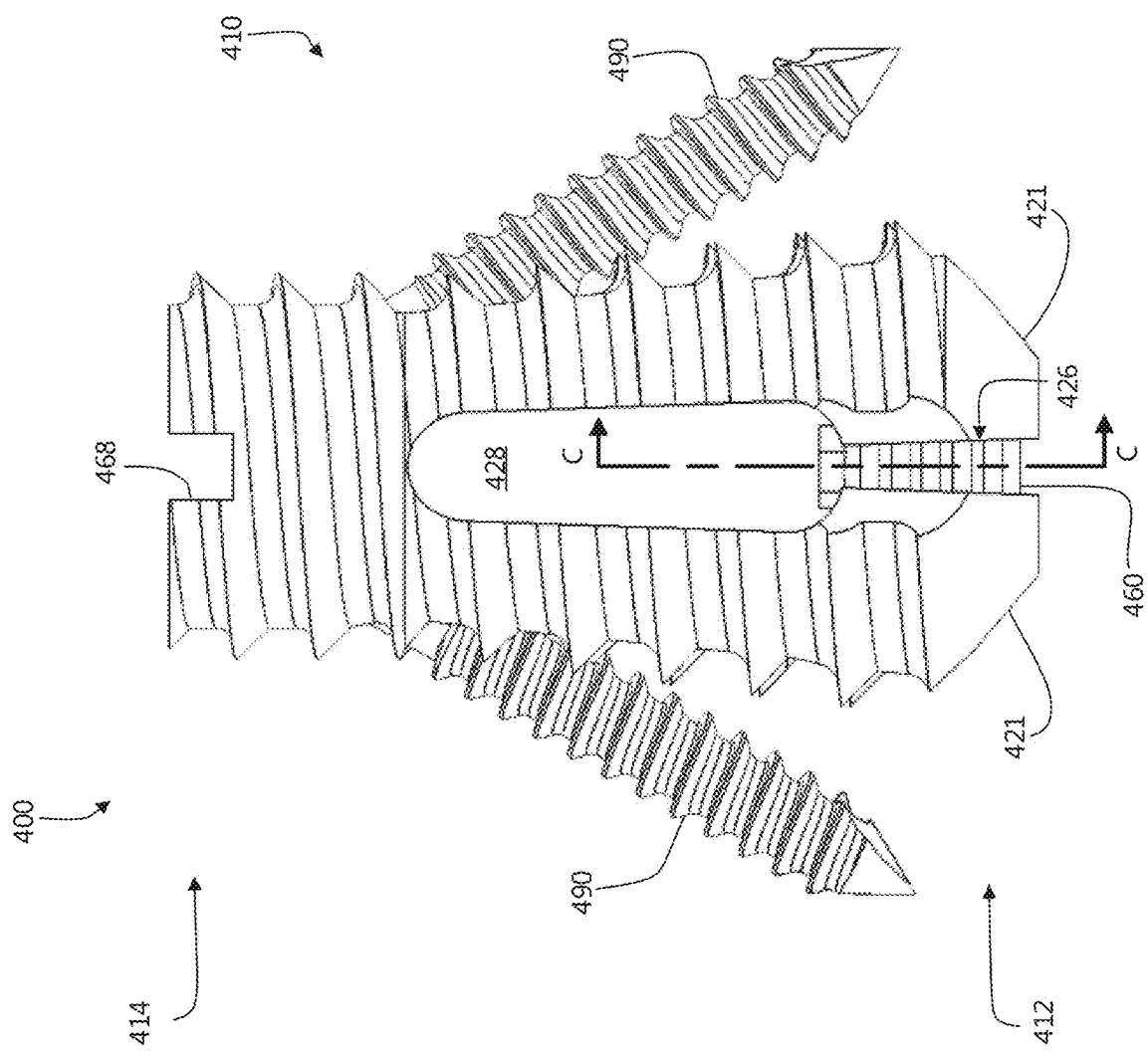
FIG. 4B illustrates a side view of the spinal fusion system of FIG. 4A.
Figure 4C:
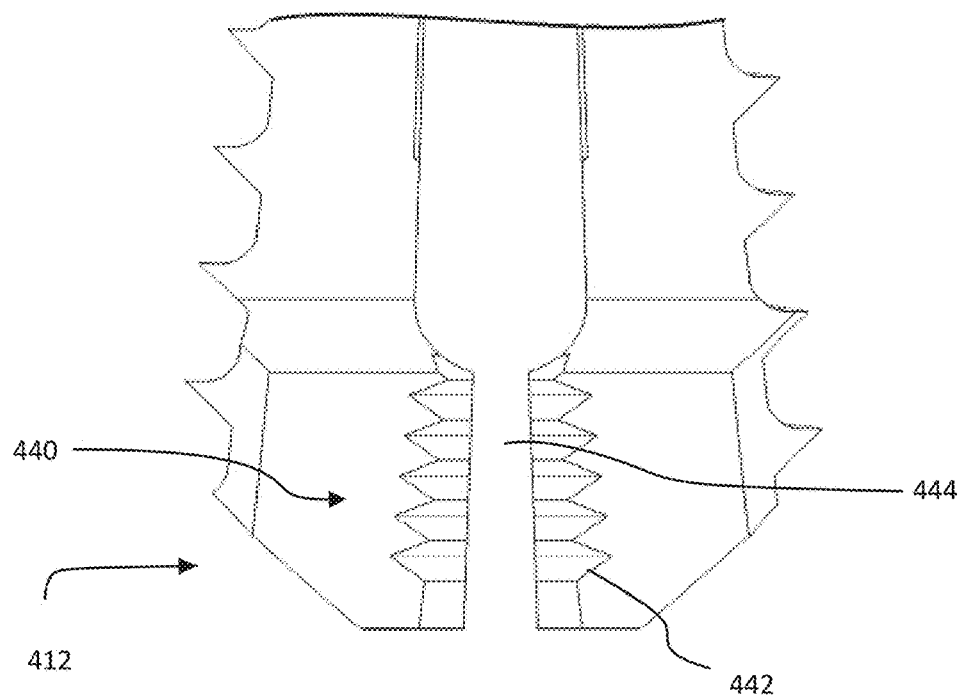
FIG. 4C illustrates a cutaway view of a section of the spinal fusion system of FIG. 4A taken from the cutting line C-C of FIG. 4B according to some embodiments.
Figure 4D:
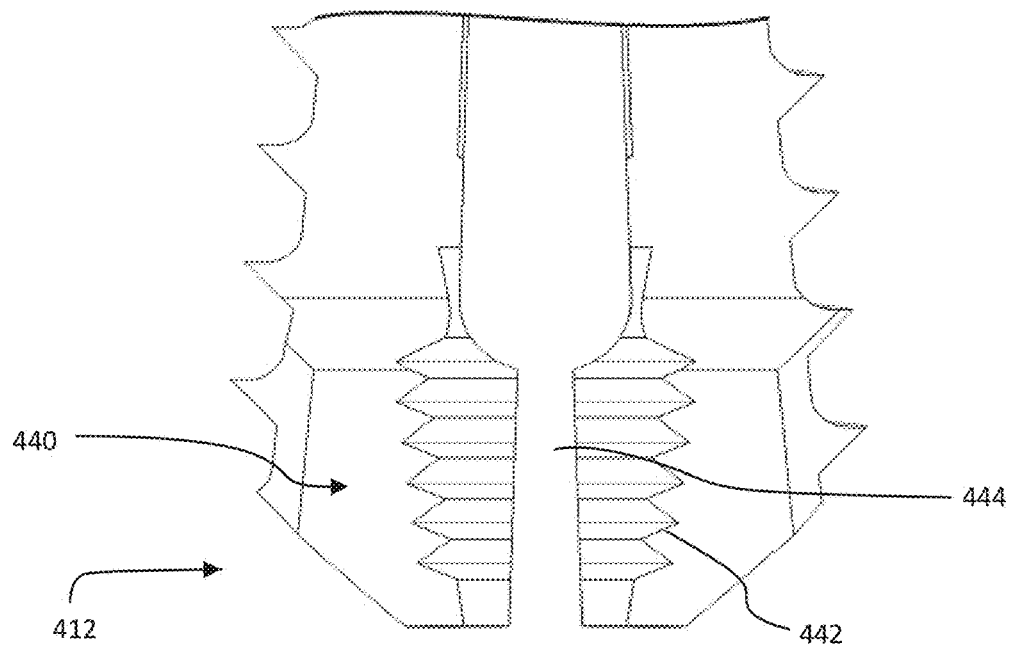
FIG. 4D illustrates a cutaway view of a section of the spinal fusion system of FIG. 4A taken from the cutting line C-C of FIG. 4B according to some embodiments.

FIGS. 4C and 4D illustrate embodiments of an expansion mechanism 440 comprising threads 442 and defining a space 444 in which the wedge 460 may be threaded. In particular, the threads 442 are formed in portions of the arms 421, 422, 423, 424. The space 444 may be a space 444 between the arms 421, 422, 423, 424 that is partially defined by the threads 444 and which may accommodate the wedge 460. The space 444 may be shaped such that a portion (e.g., an end) of the space 444 has a larger diameter than another portion of the space 444. For example, as illustrated in FIG. 4C, the size of the threads 442 (e.g., the depth of the threads 442) increases anteriorly so that an anterior portion of space 444 is larger than a posterior portion of the space 444. FIG. 4D illustrates an alternative embodiment where the size of the threads 442 decreases anteriorly so that an anterior portion of the space is smaller than a posterior portion of the space. The shape of the space 444 and overall configuration of the expansion mechanism 440 may be configured such that as the wedge 460 is advanced (or retracted) towards the portion of the space 444 having the decreasing diameter, the arms 421, 422, 423, 424 spread (e.g., due to elastic deformation in a body portion of the fusion cage 410 from which the arms extend) to accommodate the wedge 460.

Figure 4F:
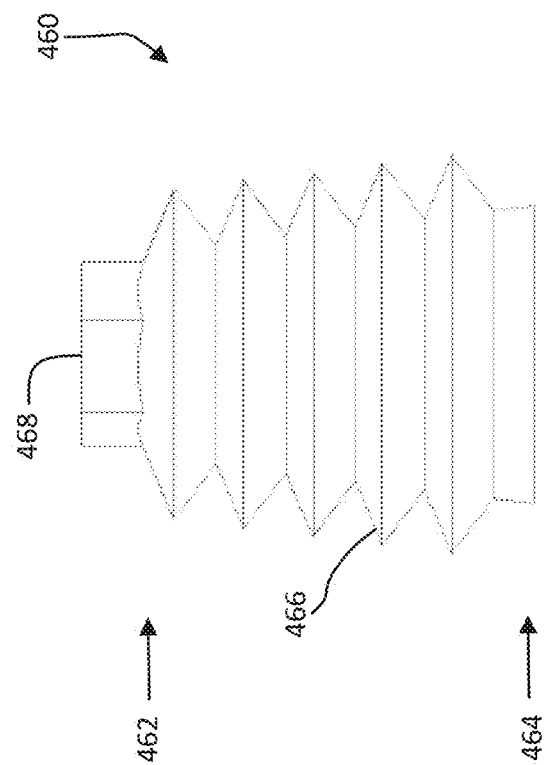
FIG. 4F illustrates a side view of the wedge of FIG. 4E.
Figure 4E:
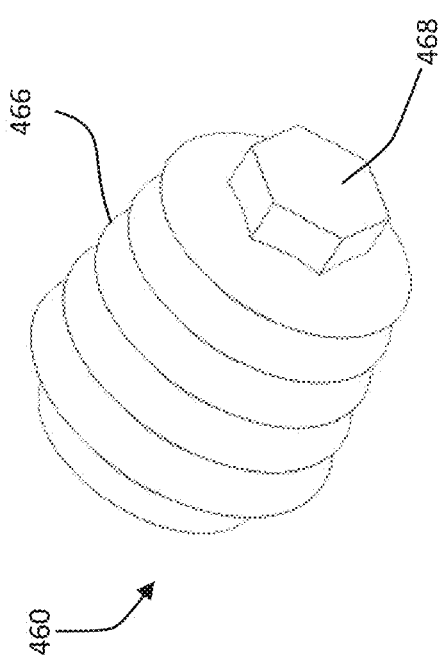
FIG. 4E illustrates a perspective view of a wedge, according to some embodiments.
Figure 4H:
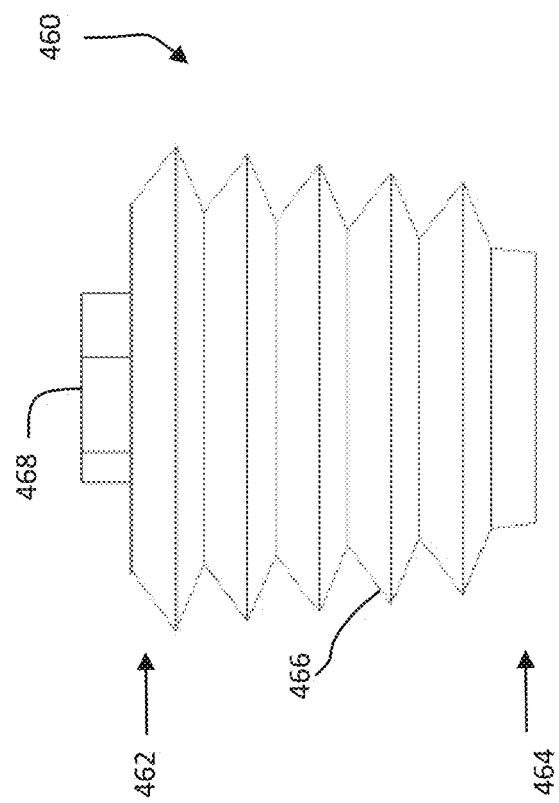
FIG. 4H illustrates a side view of the wedge of FIG. 4G.
Figure 4G:
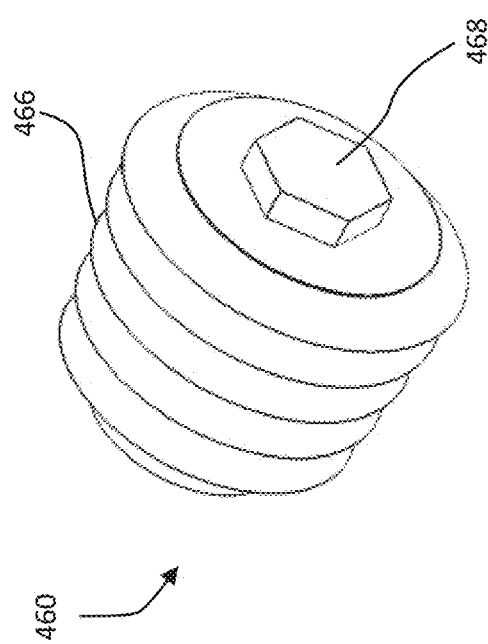
FIG. 4G illustrates a perspective view of a wedge, according to some embodiments.

FIGS. 4E-4H illustrates embodiments of the wedge 460. In particular, FIGS. 4E and 4F illustrate a wedge 460 sized and shaped to match the expansion mechanism 440 of FIG. 4C. FIGS. 4G and 4H illustrate a wedge 460 sized and shaped to match the expansion mechanism 440 of FIG. 4D. In particular, the diameter of the thread 466 of FIGS. 4E and 4F increases anteriorly, while the diameter of the thread 466 of FIGS. 4G and 4H decreases anteriorly.

While the threads 442 are illustrated as a series of landings or detents for ease of viewing, the threads 442 may be configured as an internal (female) screw thread. Similarly, while the thread 466 of the wedge 460 is illustrated as a series of portions of increased diameter, the thread 466 may be configured as an external (male) screw thread. The threads 442, 466 may be configured to be complimentary, such that the wedge 460 may be screwed into the threads 442. In some embodiments, the wedge 460 may be disposed within the expansion mechanism 440 such that, when in an unexpanded configuration, most of the thread 466 of the wedge 460 is disposed within the threads 442 of the expansion mechanism 440 (e.g., as shown in FIG. 4A). In some embodiments, the wedge 460 may begin partially or entirely outside of the space 444 and be advanced or retracted into the space 444. While the tool engagement feature 468 is illustrated as a hexagonal extension from the wedge 460, it need not be so configured. For example, in some embodiments, the tool engagement feature 468 may be recessed into the wedge 460 or take other forms. In some embodiments, the wedge 460 may be threaded towards the inside of the cage 410 (e.g., for use with the cage 410 of FIG. 4C). In some embodiments, the wedge may be threaded towards the anterior end 412 of the cage 410 (e.g., for use with the cage 410 of FIG. 4D).

In some embodiments, the fusion cage 410 may be substantially similar to previously described fusion cages 110, 210, and 310. The features may also be similar, including but not limited to the threads 116, 216, 316 the tool engagement features 118, 218, 318, the inner spaces 220, 320, the first arms 222, 322 the second arms 224, 324 the discontinuities 226, 326 the openings 228, 328, 230, 330 and other features. In addition, the illustrated embodiment of the fusion cage 410 has the tool engagement feature 440 located on the posterior end 414 and has the arms 421, 422, 423, 424 configured to spread near the anterior end 412.

The fusion cage 410 may include differences from previously described embodiments 110, 210, 310. For example, as best illustrated by FIG. 4B, the diameter of the fusion cage 410 may increase across a length of the cage 410. The diameter may increase from the anterior end 412 towards the posterior end 414 until a tip portion where the diameter decreases. The diameter of a threaded portion of the fusion cage 410 may increase along the length of the cage 410 until a thread-less tip portion is reached. such that in an initial, unexpanded configuration, the anterior end 412 has a greater diameter than the anterior end 414. As another example, there may be a plurality of discontinuities, which divide the fusion cage 410 into a plurality of arms. In particular, FIG. 4A illustrates a fusion cage 410 having two perpendicular discontinuities 426, 427 that separate four arms 421, 422, 423, 424.

The systems 100, 200, 300, 400 and fusion cages 110, 210, 310, 410 may be formed in various sizes to accommodate different patients. Various sizes may also accommodate different vertebrae within a given patient. An instrument set supplied to a surgeon may include several different sizes of systems 100, 200, 300, 400 and fusion cages 110, 210, 310, 410. The systems 100, 200, 300, 400 and devices 110, 210, 310, 410 may also be formed based on a desired amount of lordosis. For example, in situations where a comparatively large amount of lordosis is desired, the arms of the device may be configured to be spread farther than a device where a comparatively small amount of lordosis is desired. This difference in spreading may be achieved by modifying the expansion mechanism. For example, with regard to system 100, the wedge 160 may have a comparatively larger anterior end 162 diameter to encourage greater lordosis. With regard to system 200, some of the detents may have a comparatively smaller diameter. With regard to system 300, the cam 360 may be comparatively more elongate. With regard to system 400, the wedge 460 may have a comparatively larger anterior end 464 and/or the space 444 may have a comparatively smaller anterior portion.

The systems 100, 200, 300, 400 and the fusion cages 110, 210, 310, 410 may be configured to provide a surgeon multiple expansion sizes in a single cage. For example, a surgeon may be provided with a single fusion cage 110, 210, 310, 410 that may be expanded to different sizes. Such a feature may provide customizability to the operation and may reduce the number of SKUs needed to be prepared for a given operation. With regard to systems 100, 400 the surgeon may advance or retract the wedge 160, 460 until a desired amount of lordosis is created. With regard to system 200, the surgeon may advance the slider 260 into progressively smaller landings until a desired amount of lordosis is created. With regard to system 300, the fusion cage 310 may be configured with multiple detents in the cavity 342 and the surgeon may rotate the cam 360 into successive detents until a desired amount of lordosis is created.

The systems 100, 200, 300, 400, fusion cages 110, 210, 310, 410 and/or components thereof may be made of any biocompatible materials. Example materials include, but are not limited to, metals, ceramics, polymers, composites, or other suitable types of biocompatible materials. In some embodiments, the systems 100, 200, 300, 400 and fusion cages 110, 210, 310, 410 and/or components thereof are formed of titanium, titanium alloys, steel, steel alloys, or any combination thereof. One criterion for the selection of materials and for the design of particular embodiments may be based on the amount of spreading of the arms that may be desired. For example, the systems 100, 200, 300, 400 fusion cages 110, 210, 310, 410 and/or components thereof may be configured to accommodate the spreading of the arms a particular distance via elastic deformation. In some embodiments, it may be desirable to accommodate, allow for, or enable other kinds of deformation, such as plastic deformation.

In some embodiments, the fusion cages 110, 210, 310, 410 may be designed to be substantially integrally formed. For example, the fusion cages 110, 210, 310, 410 may be constructed from only a single material or constructed from multiple, separate materials that are integrally fused together.

While certain embodiments may be illustrated as having tool engagement features and the spreading of the arms occurring at particular locations, they need not be located in the illustrated locations. For instance, the arms may be configured to expand at the same or opposite end as the tool engagement features and may correspond to posterior or anterior portions of the fusion cages 110, 210, 310, 410. This may be based on various factors including a desired approach (e.g., posterior or anterior surgical approaches).

Figure 5:
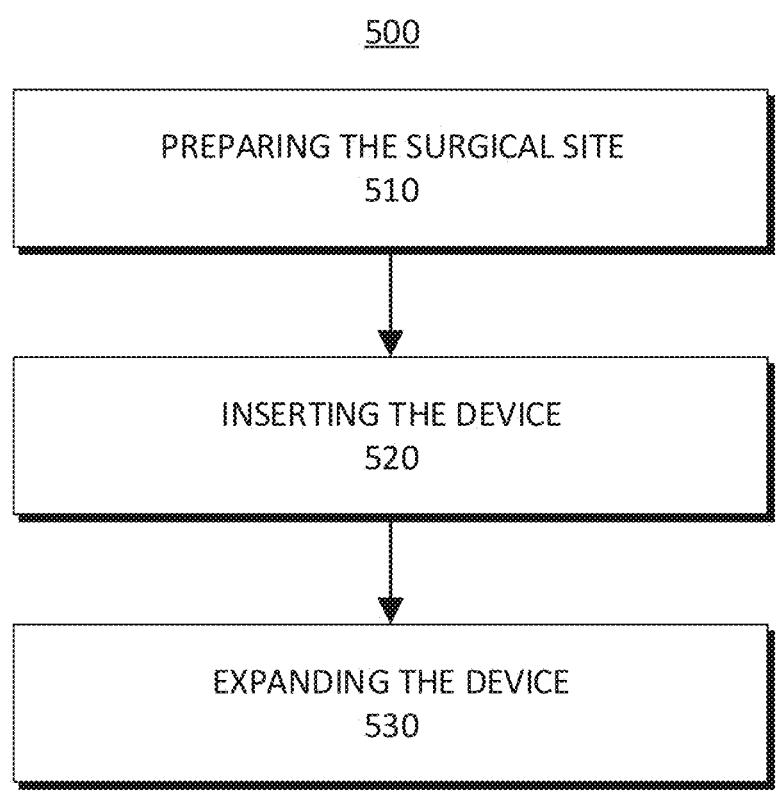
FIG. 5 illustrates a method of performing spinal fusion according to some embodiments.

FIG. 5 illustrates an example method 500 of using the systems and devices described herein to perform a spinal fusion procedure. The method may include preparing the surgical site 510, inserting the device 520, and expanding the device 530.

Preparing the surgical site 510 may be an initial step that encompasses a variety of preparatory sub-steps. For example, preparing the surgical site 510 may include selecting a patient, imaging the patient, planning surgical access approaches (e.g., posterior or anterior approaches), removing a spinal fusion system 100, 200, 300, 400 from sterile packaging (e.g., from a sterile kit comprising the fusion system 100, 200, 300, 400 and associated tools), and performing surgical access approaches to access the surgical site. This step 510 may also include steps for preparing the spine for insertion of a spinal fusion cage 110, 210, 310, 410. Preparing the spine may include, for example, removing a disk between vertebral bodies, drilling a cavity in vertebral bodies, creating a thread within the vertebral bodies, preparing the spine for receiving a fusion (e.g., removing spurs from a vertebra), separating vertebrae, inserting a bone graft material, and other preparatory steps.

Inserting the device 520 may include steps necessary for inserting a system 100, 200, 300, 400 into an appropriate location. This step 520 may involve, for example, the sub-steps of placing the spinal fusion cage 110, 210, 310, 410 at a cavity, placing a tool at a tool engagement feature (e.g., tool engagement feature 118, 218, 318, 418), and applying force to the fusion cage 110, 210, 310, 410 (e.g., applying rotational force using the tool to screw the fusion cage 110, 210, 310, 410 into the cavity).

Expanding the device 530 may include steps necessary for expanding the spinal fusion cage 110, 210, 310, 410. The sub-steps of this step 530 may vary, depending on which embodiment is used. For example, in embodiments using the system 100, this step 530 may include sub-steps of placing the posterior end 164 of the wedge 160 in the opening 130, using a tool attached to the tool engagement feature 178 to rotate the wedge 160 into the opening 130 and inner space 120, continuing to rotate the wedge 160 until the arms 122, 124 are sufficiently spread apart.

In embodiments using the system 200, the sub-steps of this step 530 may involve inserting a tool through the opening 230, placing a tool adjacent to the slider 260 (e.g., by interfacing the tool with the opening 262 in the slider 260), directly or indirectly applying expansion or contraction energy to the slider 260 using the tool until, for example, the slider keel 280 moves from a first detent to a second detent, and repeating as necessary until the arms 222, 224 are sufficiently spread. There may also be a sub-step of applying a different kind of force and causing the keel 280 to move from a second detent to a first detent to cause the arms 222, 224 to have a lessened spread.

In the embodiments using the system 300, the sub-steps of this step 530 may include inserting a tool through an opening in the fusion cage 310 (e.g., opening 320) and connecting a distal end of the tool with the tool engagement feature 378 of the cam 360, applying rotational force to rotate the cam 360 sufficient to cause elastic deformation of the fusion cage and spread the arms 322, 324. The cam 360 may be rotated in a variety of amounts including but not limited to a ⅛ turn, a ¼ turn, and a ½ turn. In some embodiments, the cam 360 may be rotated until it is arrested within a detent of the cavity 342.

In the embodiments using the system 400, the sub-steps of this step 530 may include inserting a tool through an opening in the fusion cage 410 (e.g., an opening in the posterior end 414, similar to opening 320 of fusion cage 310) and connecting a distal end of the tool with the tool engagement feature 468 of the wedge 460, applying rotational force to move the wedge 460 within the space 444, continuing to move the wedge 460 until the arms 421, 422, 423, 424 are sufficiently spread apart. The direction of motion that causes the arms 421, 422, 423, 424 to spread may depend on the configuration of the space 444. For example, in the embodiment shown in FIG. 4C, the wedge 460 is retracted posteriorly through the space 444 to spread the arms 421, 422, 423, 424. In the embodiment shown in FIG. 4D, the wedge 460 is advanced anteriorly through the space 444 to spread the arms 421, 422, 423, 424.

In some embodiments, other or additional actions may be performed. For example, a plate and screws may be installed over the graft to provider enhanced stability and fixation. In some embodiments, screws (e.g., screws 290) may be installed. The screws may be installed so as to promote fixation.

Although this invention has been disclosed in the context of certain embodiments and examples, the present invention extends beyond the specifically disclosed embodiments to other alternative embodiments and/or uses of the invention and modifications and equivalents thereof. Also, individual aspects of any embodiment can be claimed separately or in combination with aspects and features of that embodiment or any other embodiment. Thus, it is intended that the scope of the present invention herein disclosed should not be limited by the particular disclosed embodiments described above, but should be determined only by a fair reading of the claims that follow.

What is claimed is:

1. A spinal fusion system, comprising:
a fusion cage that includes:
an elongate, threaded, cylindrical body having a base portion and an expandable portion opposite the base portion, the expandable portion including a first arm and a second arm extending from and integrally and movably connected to the base portion of the cylindrical body such that the arms are spreadable from each other from an unexpanded position to an expanded position, the arms defining an inner space of the fusion cage, wherein the expandable portion further defines a first opening, wherein the base portion defines a second opening configured to receive a spinal fixation screw therethrough, the second opening being aligned with the first opening to align the fixation screw through the second opening, and wherein the first opening is positioned and shaped to allow the fixation screw to extend from the second opening, through the first opening and into a vertebra in the unexpanded position, the expanded position, and during the spreading therebetween, and
a tool engagement feature on the cylindrical body;
an expansion mechanism having an inner expansion member within the inner space, wherein the inner expansion member is associated with the arms such that rotation of the inner expansion member within the inner space causes the inner expansion member to advance toward the expandable portion of the cylindrical body and spread the arms; and
the at least one spinal fixation screw positionable through the second and first openings and configured for affixing the base portion to the vertebra while allowing the arms to be positioned in the unexpanded position, the expanded position, and during the spreading therebetween.

2. The spinal fusion system of claim 1, further comprising third and fourth arms extending from and integrally connected to the base portion of the cylindrical body,
wherein the inner space is between the first, second, third, and fourth arms; and
wherein, the inner expansion member is configured to spread the first, second, third, and fourth arms radially away from each other and the at least one spinal fixation screw.

3. The spinal fusion system of claim 1, wherein the tool engagement feature is located at the base portion of the cylindrical body.

4. The spinal fusion system of claim 1, wherein:
the inner expansion member comprises first threads;
the first arm and the second arm comprise second threads within the inner space; and
the first threads and the second threads are complimentary threads.

5. The spinal fusion system of claim 4, further comprising a wherein the first opening is further defined between the first and second arms and extending into the inner space, wherein the inner expansion member has a diameter that is greater than a diameter of the first opening.

6. The spinal fusion system of claim 4, wherein at least one of the first threads or the second threads is tapered.

7. The spinal fusion system of claim 1, wherein the inner expansion member comprises a cam disposed within the inner space such that the cam spreads the first and second arms responsive to the cam rotating a first distance.

8. The spinal fusion system of claim 7, wherein the cam has an elliptic cylinder shape.

9. The spinal fusion system of claim 7, wherein the cam is disposed within the inner space in a first position, and wherein at least one detent is positioned within the inner space and configured to arrest the motion of the cam after the cam is rotated a pre-determined distance.

10. The spinal fusion system of claim 7, wherein the tool engagement feature is located at the base portion of the cylindrical body.

11. The spinal fusion system of claim 7, wherein the base portion of the cylindrical body comprises a frustoconical tip.

12. The spinal fusion system of claim 7, wherein the first distance is ¼ turn of the cam.

13. The spinal fusion system of claim 1, wherein said rotation of the inner expansion member causes elastic deformation of the first and second arms.

14. The spinal fusion system of claim 1, wherein:
the inner expansion member comprises a wedge defining exterior threads;
the first arm and the second arm cooperate to define interior threads within the internal space; and
the exterior threads are configured to engage the interior threads and deform the arms at the expandable portion.

15. The spinal fusion system of claim 14, wherein:
the spinal fusion system further comprises third and fourth arms extending longitudinally from the base portion of the cylindrical body to the expandable portion of the cylindrical body; and
the first, second, third, and fourth arms are separated from one another at the expandable portion.

16. The spinal fusion system of claim 15, wherein the first, second, third, and fourth arms are arranged to spread radially away from one another and the spinal fixation screw in response to the rotation of the inner expansion member.

17. The spinal fusion system of claim 1, wherein the tool engagement feature is configured to receive a rotational input that advances the inner expansion member toward the expandable portion.

18. The spinal fusion system of claim 1, wherein the first and second arms define the first opening therebetween.

19. The spinal fusion system of claim 1, wherein the first opening extends through one of the arms.

20. The spinal fusion system of claim 1, wherein:
the at least one spinal fixation screw includes a screw head and a screw shaft extending from the screw head; and
the second opening is adapted to receive the screw shaft and has a size that is smaller than a size of the screw head such that the base is affixable by the screw head.

21. The spinal fixation system of claim 20, wherein the screw head is in engaged contact with the base portion, and the screw shaft is arranged through the second opening and separated from the expandable portion.

22. The spinal fixation system of claim 20, wherein the screw head is disposed entirely within the base portion.

23. The spinal fixation system of claim 1, wherein the second opening extends into the inner space, and the inner space is configured to receive a surgical tool to access both the at least one spinal fixation screw and expansion member.

* * * * *